US009424958B2

(12) United States Patent
Vogtmeier et al.

(10) Patent No.: US 9,424,958 B2
(45) Date of Patent: Aug. 23, 2016

(54) MULTIPLE FOCAL SPOT X-RAY RADIATION FILTERING

(75) Inventors: Gereon Vogtmeier, Aachen (DE); Rainer Pietig, Maisch (DE); Christoph Loef, Aachen (DE); Martin Kimutai Duerr, Aachen (DE); Gerald James Carlson, Aurora, IL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 196 days.

(21) Appl. No.: 14/117,869

(22) PCT Filed: May 30, 2012

(86) PCT No.: PCT/IB2012/052703
§ 371 (c)(1),
(2), (4) Date: Nov. 15, 2013

(87) PCT Pub. No.: WO2012/168832
PCT Pub. Date: Dec. 13, 2012

(65) Prior Publication Data
US 2014/0105361 A1    Apr. 17, 2014

Related U.S. Application Data

(60) Provisional application No. 61/493,556, filed on Jun. 6, 2011.

(51) Int. Cl.
*G21K 1/08* (2006.01)
*G21K 1/10* (2006.01)
*G21K 1/02* (2006.01)
(Continued)

(52) U.S. Cl.
CPC *G21K 1/08* (2013.01); *G01N 23/04* (2013.01);
*G21K 1/025* (2013.01); *G21K 1/10* (2013.01);
*H01J 35/08* (2013.01); *H01J 35/30* (2013.01)

(58) Field of Classification Search
CPC ......... G01N 23/04; G21K 1/025; G21K 1/08;
G21K 1/10; H01J 35/08; H01J 35/30; H01J 35/24; H01J 35/305
See application file for complete search history.

(56) References Cited

U.S. PATENT DOCUMENTS

| 2,638,554 | A | 5/1953 | Bartow et al. |
| 4,821,306 | A | 4/1989 | Mulder |

(Continued)

FOREIGN PATENT DOCUMENTS

| JP | 2008012206 A | 1/2008 |
| JP | 200928405 A | 2/2009 |

(Continued)

*Primary Examiner* — Wyatt Stoffa

(57) ABSTRACT

For the generation of multiple-energy X-ray radiation, an X-ray tube (10) for generating multiple-energy X-ray radiation includes an anode (12) and a filter (14). At least a first (16) and a second focal spot position (18) are offset from each other in an offset direction (20) transverse to an X-ray radiation projection direction. The filter includes a first plurality (22) of first portions (24) with first filtering characteristics for X-ray radiation and a second plurality (26) of second portions (28) with second filtering characteristics for X-ray radiation. The filter is a directional filter adapted in a such a way that at least a first X-ray beam (30) emanating from the first focal spot position at least partly passes through the filter unit via the first portions, and a second X-ray beam (32) emanating from the second focal spot position passes obliquely through the first and the second portions when passing through the filter unit.

16 Claims, 20 Drawing Sheets

(51) Int. Cl.
  *G01N 23/04* (2006.01)
  *H01J 35/08* (2006.01)
  *H01J 35/30* (2006.01)

(56) References Cited

U.S. PATENT DOCUMENTS

| | | | |
|---|---|---|---|
| 6,683,934 B1 | 1/2004 | Zhao et al. | |
| 8,520,803 B2 * | 8/2013 | Behling | H01J 35/10 378/124 |
| 8,687,769 B2 * | 4/2014 | Behling | H01J 35/06 378/124 |
| 8,953,746 B2 * | 2/2015 | Roshi | H01J 35/06 378/125 |
| 2003/0147502 A1 * | 8/2003 | Heismann | A61B 6/032 378/156 |
| 2004/0247082 A1 * | 12/2004 | Hoffman | A61B 6/032 378/119 |
| 2005/0084073 A1 | 4/2005 | Seppi et al. | |
| 2008/0063145 A1 | 3/2008 | Hamill | |
| 2008/0247504 A1 | 10/2008 | Edic et al. | |
| 2009/0028292 A1 * | 1/2009 | Popescu | A61B 6/032 378/19 |
| 2009/0161815 A1 * | 6/2009 | Grass | A61B 6/032 378/5 |
| 2010/0074393 A1 * | 3/2010 | Thran | G21K 1/10 378/4 |
| 2010/0111388 A1 * | 5/2010 | Seppi | A61B 6/032 382/130 |
| 2010/0278296 A1 | 11/2010 | Edic et al. | |
| 2012/0163530 A1 * | 6/2012 | Sainath | A61B 6/027 378/5 |
| 2013/0266115 A1 * | 10/2013 | Fan | A61B 6/06 378/16 |

FOREIGN PATENT DOCUMENTS

| | | |
|---|---|---|
| WO | 2008068690 A2 | 6/2008 |
| WO | 2009017348 A2 | 2/2009 |

* cited by examiner

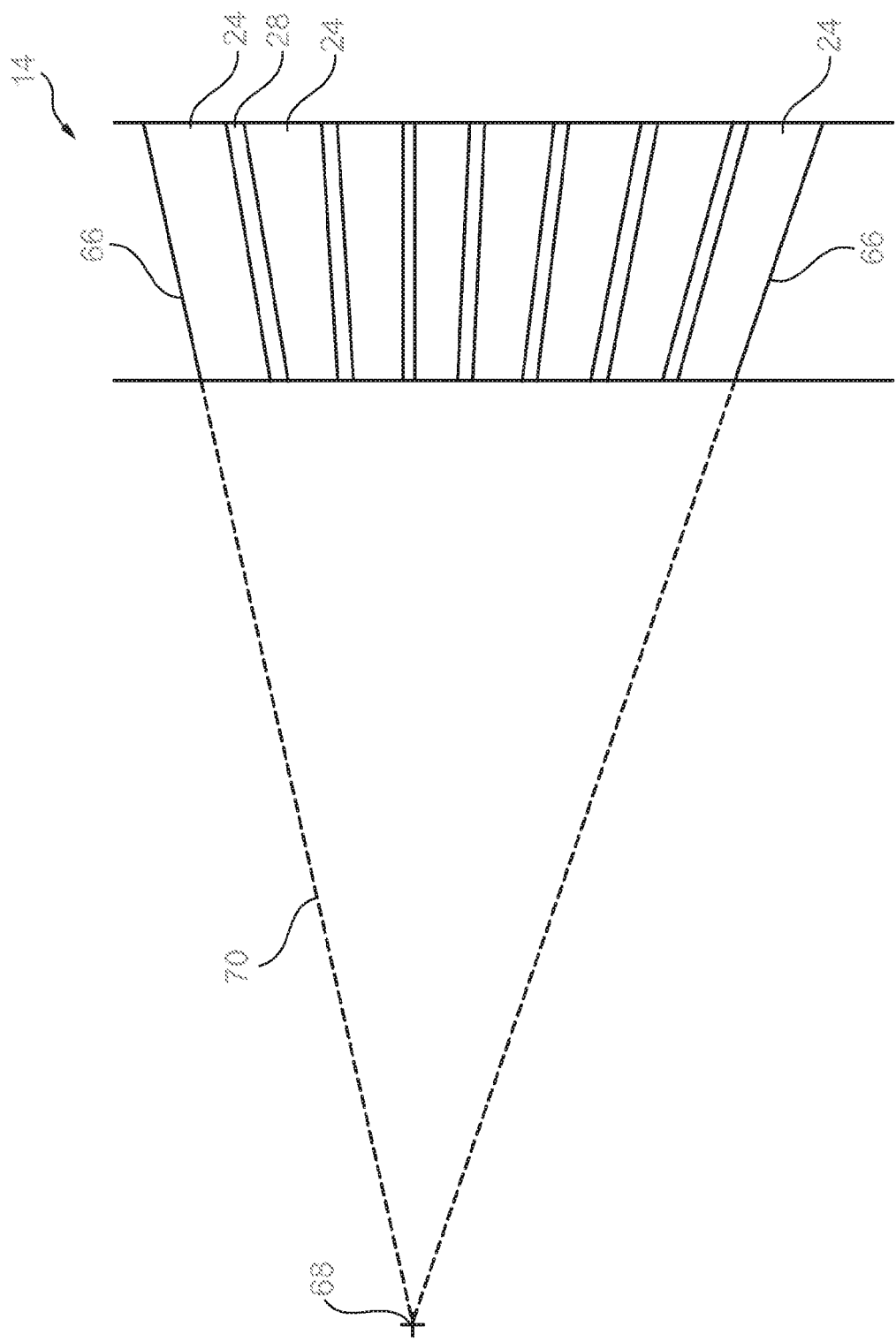

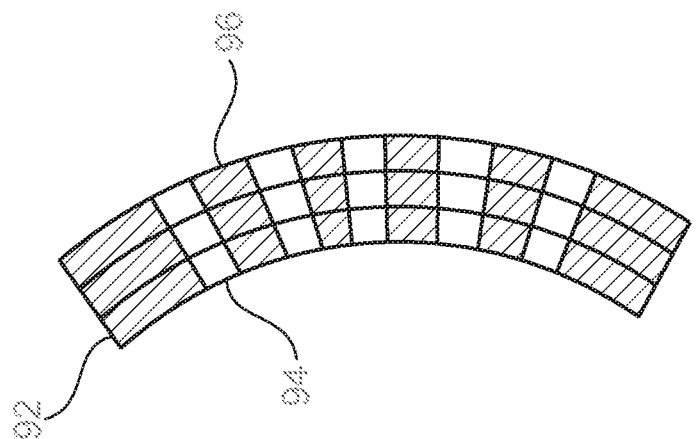
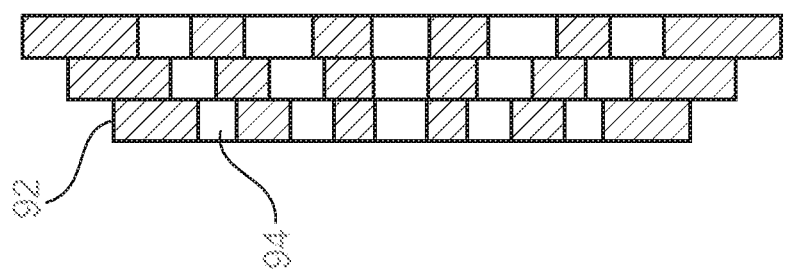
Fig. 11

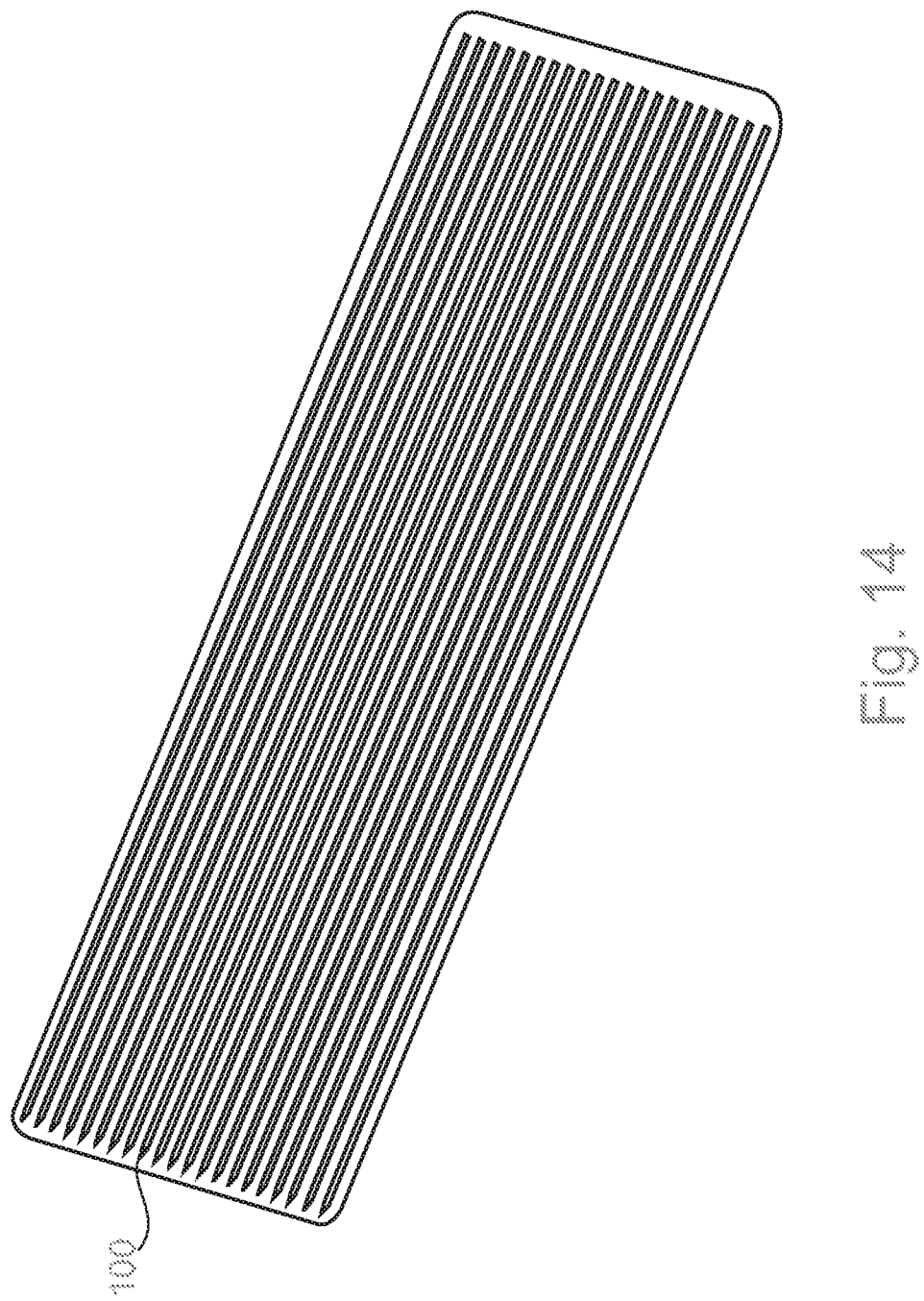

MULTIPLE FOCAL SPOT X-RAY RADIATION FILTERING

This application is a national stage application under 35 U.S.C. §371 of International Application No. PCT/IB2012/052703 filed on May 30, 2012 and published in the English language on Dec. 13, 2012 as International Publication No. WO/2012/168832, which claims priority to U.S. Application No. 61/493,556 filed on Jun. 6, 2011, the entire disclosures of which are incorporated herein by reference.

FIELD OF THE INVENTION

The present invention relates to filtering of X-ray radiation generated at multiple focal spots. The present invention relates in particular to an X-ray tube for generating multiple-energy X-ray radiation, an X-ray imaging system, a method for generating a multiple-energy X-ray beam, and a computer program element as well as a computer readable medium. The present invention also relates to a use of a filter unit for the generation of multiple X-ray radiation.

BACKGROUND OF THE INVENTION

The use of multiple-energy, in particular dual-energy, is increasing rapidly, for example, in medical imaging. Multiple-energy X-ray radiation can provide increased contrast in images as well as in material composition identification. An example for an approach to achieve the desired spectral separation is kV switching, generating X-ray beams of differing energy. Another example is two separate X-ray sources with different filters. However, this implies increased costs and a complicated constructional setup.

SUMMARY OF THE INVENTION

It is an object of the present invention to provide additional possibilities for the generation of multiple-energy X-ray radiation.

It should be noted that the following described aspects of the invention apply also for the X-ray tube for generating multiple-energy X-ray radiation, the X-ray imaging system, the method for generating a multiple-energy beam, the computer program element, and the computer readable medium as well as the use of a filter unit for the generation of multiple X-ray radiation.

According to a first aspect of the present invention, an X-ray tube for generating multiple-energy X-ray radiation is provided with an anode and a filter unit. The anode comprises at least a first and a second focal spot position, which are offset from each other in an offset direction transverse to X-ray radiation projection direction. The filter unit comprises a first plurality of first portions with first filtering characteristics for X-ray radiation and a second plurality of second portions with second filtering characteristics for X-ray radiation. The filter unit is a directional filter adapted in such a way that at least a first part of a first X-ray beam emanating from the first focal spot position at least partly passes through the filter unit via the first portions, and at least a second part of a second X-ray beam emanating from the second focal spot position passes the second portions when passing through the filter unit. The second part of the second X-ray beam is larger than the first part of the first X-ray beam. A portion of the parts of the first X-ray beam, which pass through the filter unit via the first portions, and a portion of the second X-ray beam, which passes the second portions when passing through the filter unit, pass through a common area of the filter unit.

The offset direction may also be defined as lateral to the X-ray radiation projection direction.

The filter unit is a direction specific filter. For example, the first filtering characteristics are adapted to have little or no filtering effect on X-ray radiation, and the first X-ray beam generally passes the filter unit unfiltered.

According to the invention, the filter unit is assigned to the tube, e.g. an integrated part of the tube, for example, inside the tube, attached to the tube or otherwise connected to the tube. In any case the filter unit is arranged before an object radiated with the multiple X-ray radiation provided by the filter unit. In other words, the object is arranged between the filter unit and a detector.

For example, the second part of the second X-ray beam emanating from the second focal spot position passes the second portions in an inclined angle to the orientation of the first portions when passing through the filter unit, whereas the X-ray beam emanating from the first focal spot position has a smaller percentage of its X-rays passing in an inclined angle.

The second X-ray beam may pass the second portions when passing through the filter unit; for example, the complete part of the generated X-ray beam that is radiated towards the detector. Of course, X-ray radiation is generated at the focal spot in a variety of directions; however the term "X-ray beam" in this context refers to the X-rays radiated towards the detector.

According to a further exemplary embodiment, the X-ray tube is a dual-energy tube comprising a cathode arrangement, which is configured to provide an electron beam, i.e. a beam of accelerated electrons, with a first accelerating voltage to the first focal spot and an electron beam with a second accelerating voltage to the second focal spot, wherein the first voltage is lower than the second voltage. The second filter characteristics are adapted to remove low energy photons from the second voltage beam.

According to a further exemplary embodiment, the anode is a rotating anode with a rotation axis and the X-ray beam for X-ray projection is emitted in a direction perpendicular to the rotation axis. The second focal spot position is offset to the first focal spot position in a first offset direction, which is perpendicular to the rotation axis and perpendicular to the emitting direction, and/or in a second offset direction, which is perpendicular to the X-ray radiation (projection) direction and parallel to the rotation axis.

The term "perpendicular to the rotation axis" of the X-ray beam refers to an imaginary centre line of the beam and comprises also directions which are not in 90 degrees but in smaller or larger angle, for example an angle range of approximately 30 degrees to 150 degrees.

According to a further exemplary embodiment, the X-ray tube comprises an envelope and the filter unit is arranged inside the envelope or outside of an X-ray window of the envelope.

According to a further exemplary embodiment, the filter unit is removably fixed in relation to the focal spot positions.

According to a second aspect of the invention, an X-ray imaging system is provided, comprising an X-ray source and an X-ray detector. The X-ray source comprises an X-ray tube according to one of the above mentioned aspects, embodiments and examples. The X-ray detector is adapted to detect X-ray radiation resulting from the first X-ray beam emanating from the first focal spot position, and from the second X-ray beam emanating from the second focal spot position.

According to a third aspect of the present invention, a method for generating multiple-energy X-ray beam is provided, comprising the following steps:

a) generating a beam of accelerated electrons (electron beam);

b) directing the electron beam such that the electron beam impinges at a first focal spot position and at a second focal spot position of an X-ray tube in an alternating manner, wherein:

b1) a first X-ray beam is emanating from the first focal spot position, and b2) a second X-ray beam is emanating from the second focal spot position;

c) passing of the first and second X-ray beam through a filter unit, wherein:

c1) at least a first part of the first X-ray beam passes through first portions of the filter unit, and c2) at least a second part of the second X-ray beam passes second portions.

The second part of the second X-ray beam is larger than the first part of the first X-ray beam.

The first portions are provided with first filtering characteristics for the X-ray radiation and the second portions are provided with second filtering characteristics for X-ray radiation.

According to an exemplary embodiment, in step a), the electron beam is provided as a dual-energy electron beam with a first accelerating voltage to the first focal spot and with a second accelerating voltage to the second focal spot, wherein the first voltage is lower than the second voltage. In step c2), the second portions remove low energy photons from the second high voltage beam.

According to an aspect of the present invention, a dynamic focal spot is combined with a directional filter, such that X-ray radiation from one focal spot are subject to one filtering characteristic, and X-ray beam from another focal spot are subject to another filtering characteristic. Of course, this also applies for filtering only a part of the respective beam. In such case, the parts filtered with first characteristics must be higher for the first beam and lower for the second beam. Vice versa, the parts filtered with second characteristics must be lower for the first beam and higher for the second beam. Thus it is possible, for example, to provide two differently filtered X-ray beams, and hence X-ray beams with differing energies to examine an object of interest, for example a patient or also goods such as luggage or the like. The directional filter according to the present invention provides first portions with first filtering characteristics such that the X-rays generated at the respective first focal spot position generally pass through while only being subject to the first filtering characteristics, for example they generally pass through unfiltered. X-rays generated at the other focal spot positions do not have a line of sight through the first portions, and are therefore crossing second portions with second filtering characteristics, thus getting filtered by the second filtering characteristics. The energies difference can be further improved by generating X-ray beams with differing energies at the different focal spots, for which it is provided to apply differing voltages between the anode (target) and the cathode from which the electron beam is emitted. Thus, the different filtering can provide additional differences concerning the energies of the X-ray beams that are provided by the X-ray tube according to the present invention. A still further improvement is provided, according to another aspect of the present invention, by providing different target materials at the different focal spot positions. Of course, it is also possible to provide different target materials and an electron beam with a single voltage instead of switched voltages.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

FIGS. 6 to 14 show aspects of exemplary embodiments of a filter unit according to the present invention.

DETAILED DESCRIPTION OF EMBODIMENTS

Figure 1:
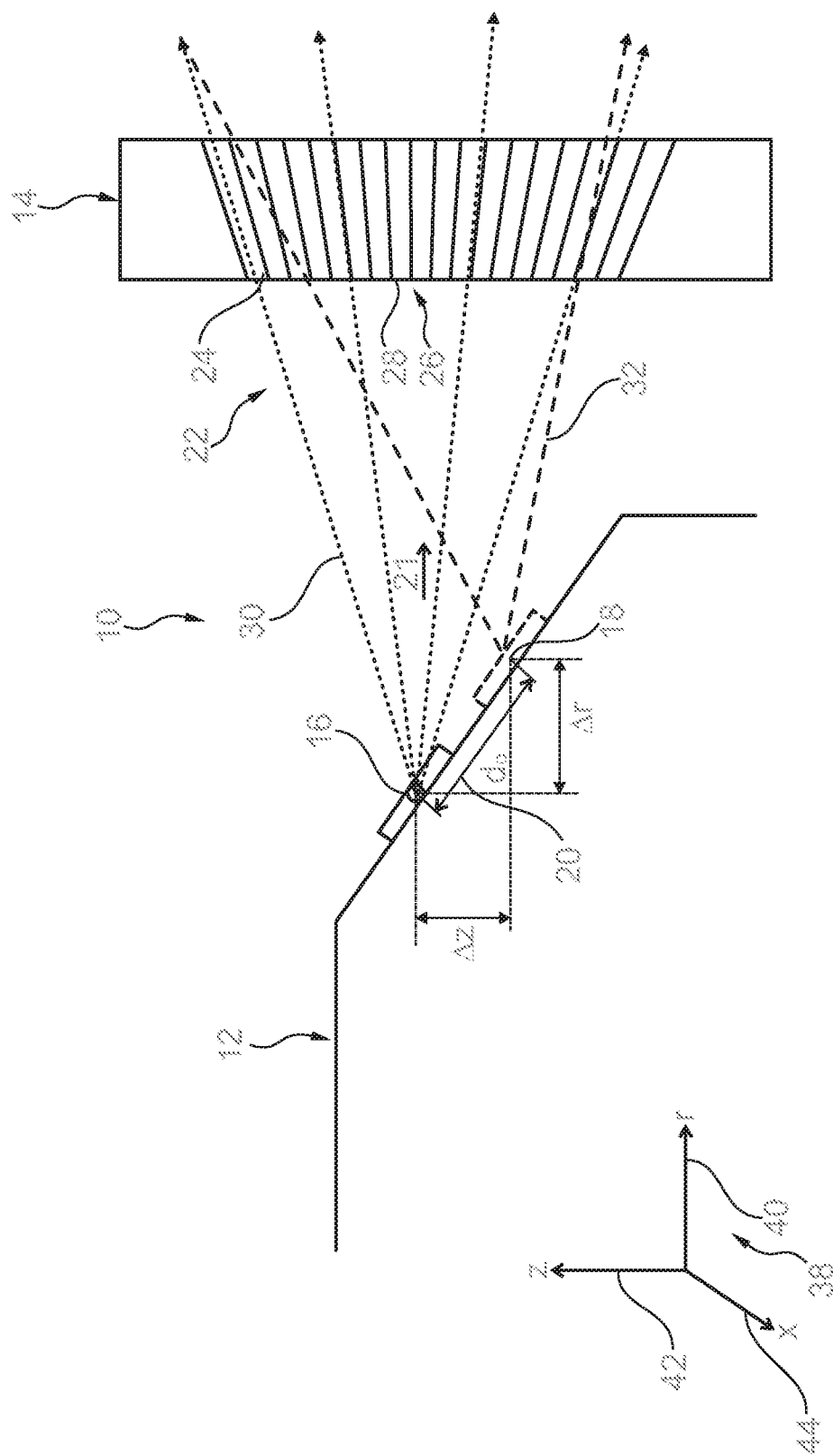
FIG. 1 illustrates an X-ray tube for generating multiple-energy X-ray radiation according to an exemplary embodiment of the invention.

FIG. 1 shows an X-ray tube 10 for generating multiple-energy X-ray radiation. The X-ray tube 10 comprises an anode 12 and a filter unit 14.

The anode comprises at least a first focal spot position 16 and a second focal spot position 18, which are offset from each other in an offset direction do, which is indicated with double arrow 20 and which is transverse an X-ray radiation projection direction 21. The term "X-ray radiation projection direction" refers to an imaginary centre line of an X-ray beam, i.e. to the main direction of the X-ray beam.

According to a further example, the "main direction" is directed towards the centre of the detector, for example from the first focal spot to the centre of the detector.

According to another example, the "main direction" is a direction from the second focal spot to the centre of the detector.

According to another example, the "main direction" is a direction from a point between the two focal spots to the centre of the detector.

The filter unit 14 comprises a first plurality 22 of first portions 24 with first filtering characteristics for X-ray radiation and a second plurality 26 of second portions 28 with second filtering characteristics for X-ray radiation. The filter unit 14 is a directional filter adapted in such a way that at least a first part of a first X-ray beam, indicated with dotted lines 30 in FIG. 1, emanating from the first focal spot position 16 passes through the filter unit 14 via the first portions 24.

With respect to FIGS. 1 to 4, it is noted that according to one example, the angled lines in the filter indicating first and second portions point to the centre of the first focal spot so that the rays from this point are parallel to these angled lines.

Figure 2:
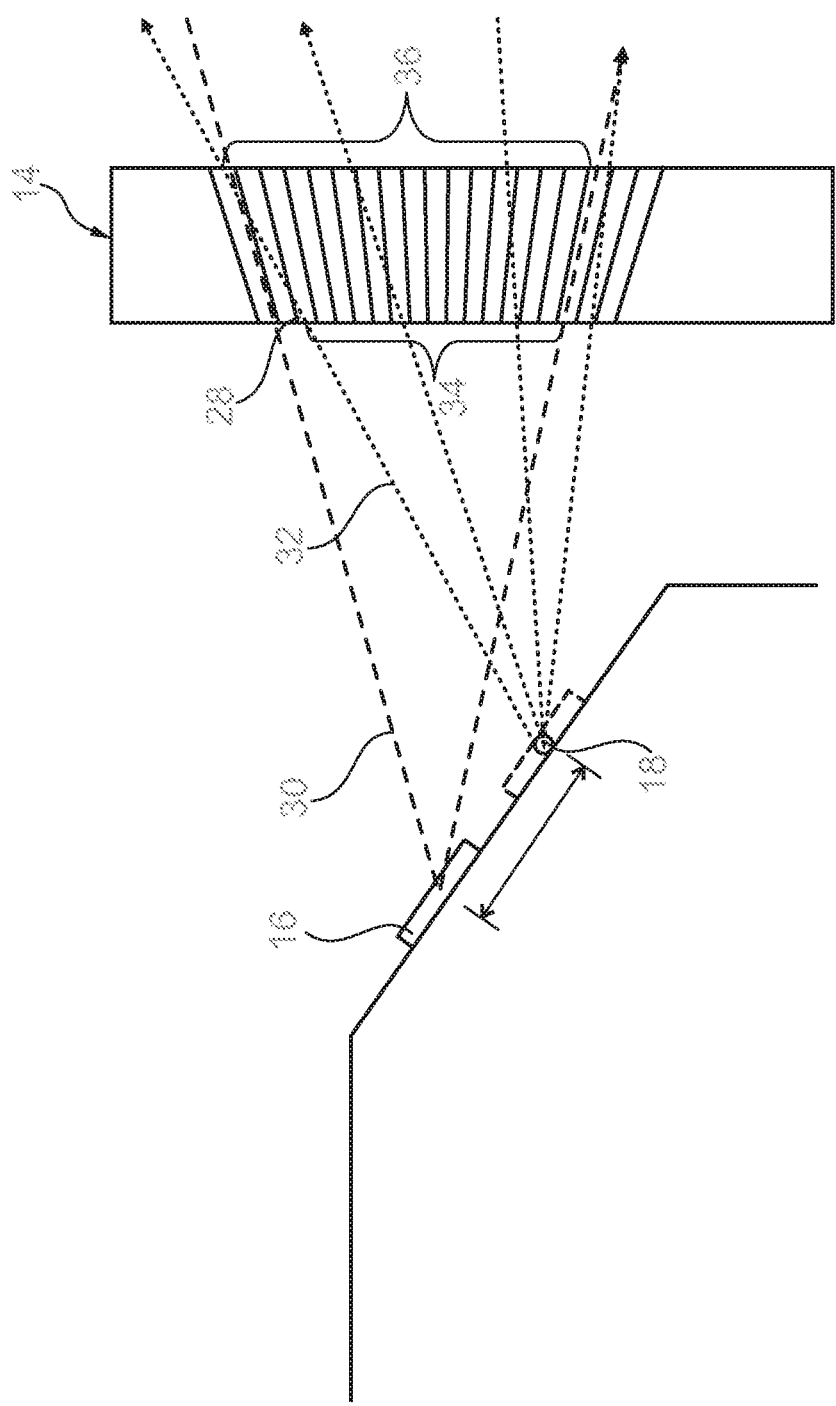
FIG. 2 illustrates a further view of the X-ray tube according to FIG. 1.

In FIG. 2, it is shown that the filter unit 14 is adapted in such a way that at least a second part of a second X-ray beam, indicated with dotted arrows 32, emanating from the second focal spot position 18 passes the second portions 28 when passing through the filter unit 14.

According to the invention, the second part of the second X-ray beam is larger than the first part of the first X-ray beam.

According to a further example, not shown, the second part of the second X-ray beam emanating from the second focal spot position passes the second portions in an inclined angle when passing through the filter unit.

According to a still further example, not shown, second X-ray beam may pass the second portions when passing through the filter unit; for example, the complete part of the generated X-ray beam that is radiated towards the detector. Of course, X-ray radiation is generated at the focal spot in a variety of directions; however the term "X-ray beam" in this context refers to the X-rays radiated towards the detector.

According to a further example, also not shown, the first portions are narrower. For example, the first portions are provided in a smaller area of the filter unit, for example, with respect to the drawing, they might not reach down as far as shown in FIG. 1.

According to a further example, not shown, the filtering effect is adapted according to the relation of the orientation of the first potions to the target angle, for example, an inclined surface on which the focal spots are located. For example, low energy photons may be "filtered" due to the Heel effect in the radiation angles that become parallel or near the target angle.

Thus, with reference to both FIG. 1 and FIG. 2, the portion of the parts of the first X-ray beam 30 which pass through the filter unit 14 via the first portions 24, and a portion of the second X-ray beam 32, which passes the second portions 28 when passing through the filter unit 14, pass through a common area of the filter unit 14.

For a better understanding, the first X-ray beam 30 is indicated in FIG. 2 with dashed outlines, and the second X-ray beam 32 is also indicated in FIG. 1 with dashed outlines.

As can be seen, the resulting common area is indicated in FIG. 2 with a left bracket 34 on the left side of the filter unit 14 and a right bracket 36 on the right side of the filter unit 14, to indicate at least the outer boundaries of the common area.

With reference back to FIG. 1, a coordinate system 38 indicates an X-ray radiation projection direction 40, also referred to as y direction, or r-axis, a first perpendicular axis 42, referred to a z-axis, and a second perpendicular axis 44, also referred to as x-axis. Thus, the offset as indicated with double arrow 20 has an r-component, i.e. an offset in the r-axis direction, which is indicated with $\Delta r$ in FIG. 1, and a z-component, i.e. the offset comprises a certain distance in z-direction, which is indicated with $\Delta z$.

With respect to the filter unit 14, the focal spot positions are provided on an inclined or slanted surface of the anode 12.

The anode may also be provided with stepwise arranged surfaces for the first and second focal spot positions (not shown), for example, instead of the inclined surface. For example, the anode may comprise a stepped edge contour with continuously provided step portions.

According to another example (not shown), the anode may also comprise an edge contour with a crenellate-type structure, for example when the anode is a rotating anode, upper and lower surfaces may thus be provided in alternating manner when rotating the anode. Thus, different focal spot positions could be provided with respect to the filter unit, however without the necessity for a respective deflection of the X-ray beam, since the X-ray beam is impinging at the same location with respect to the anode, but due to the rotational movement of the anode, the respective focal spot position is provided with different heights, thus providing the two focal spot positions being offset to each other.

According to a further exemplary embodiment (not shown), the first and second focal spot provided at the first and second focal spot positions 16, 18 comprise a first and a second target material, respectively.

According to a further aspect (also not shown), more than two focal spots are provided, which may comprise more than two different focal track materials.

Figure 3:
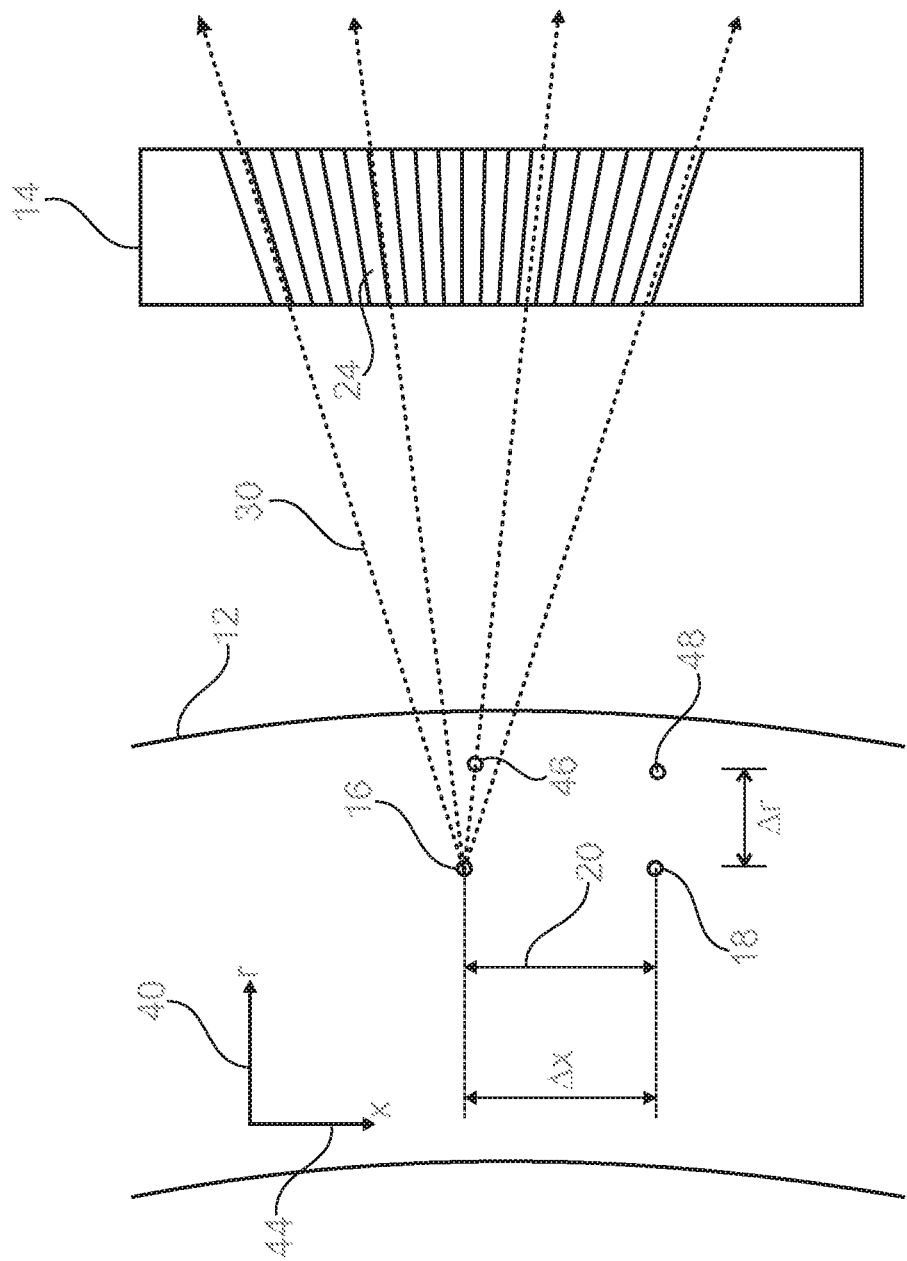
FIG. 3 illustrates an X-ray tube according to a further exemplary embodiment of the invention.

As shown in FIG. 3, the anode 12 is shown from above, i.e. with respect to the drawing of FIGS. 1 and 2. In other words, the slanted or inclined surface is now seen from above.

The first focal spot position 16 and the second focal spot position 18 are offset from each other, as indicated with double arrow 20. As indicated by a respective two axes coordinate system, indicating the radiation direction 40 and the second perpendicular axis 44, the offset is provided in the x-direction, as indicated with $\Delta x$. Thus, compared to the arrangement of FIG. 1, the offset is provided in a perpendicular direction, namely not in the z-direction, but in the x-direction. Thus, the same type of filter unit 14 can be provided, only rotated in 90 degrees.

For a further understanding, the second focal spot position of FIGS. 1 and 2 is indicated with a dotted circle 46.

According to a further exemplary embodiment, the offset is provided in z-direction as well as in x-direction, which is indicated by a second dotted circle 48.

Figure 4:
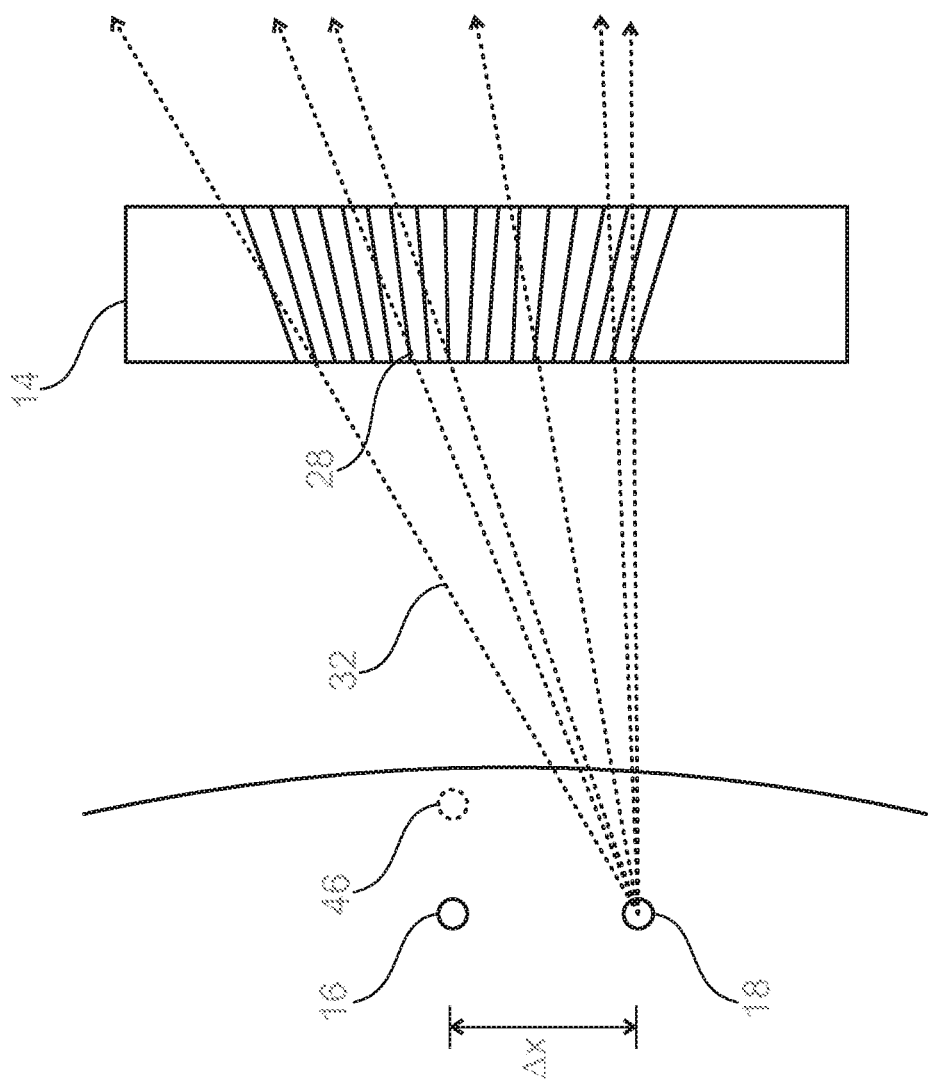
FIG. 4 illustrates a further view of the X-ray tube according to FIG. 3.

If the X-ray radiation is generated at the second focal spot position 18, as shown in FIG. 4, the second X-ray beam 32 emanates from the second focal spot position 18 and passes the second portions 28 when passing through the filter unit 14.

When the X-ray radiation is provided as the first X-ray beam 30 emanating from the first focal spot position 16, as shown in FIG. 3, the X-ray beam 30 at least partly passes through the filter unit 14 via the first portions 24.

It must be mentioned that the provision of the first portions and the second portions is provided in relation to the locations of the first and second focal spot positions, respectively.

The first X-ray beam 30 may thus essentially pass through the filter unit 14 via the first portions 24.

For example, the first filtering characteristics are adapted to have no filtering effect on X-ray radiation, such that the first X-ray beam 30 generally, or essentially, passes the filter unit 14 unfiltered.

As mentioned before, the first portions 24 are be oriented such that X-rays from the first focal spot position pass the filter unit 14 through the first portions 24.

It must be noted that more than two focal spot positions can be provided, wherein the filter is adapted such that from each focal spot, a different filter characteristic is applied to a respective X-ray beam passing through the filter unit. For example, more than two filter materials may be provided, i.e. more than two different pluralities of different portions are provided for the filter unit.

Figure 5:
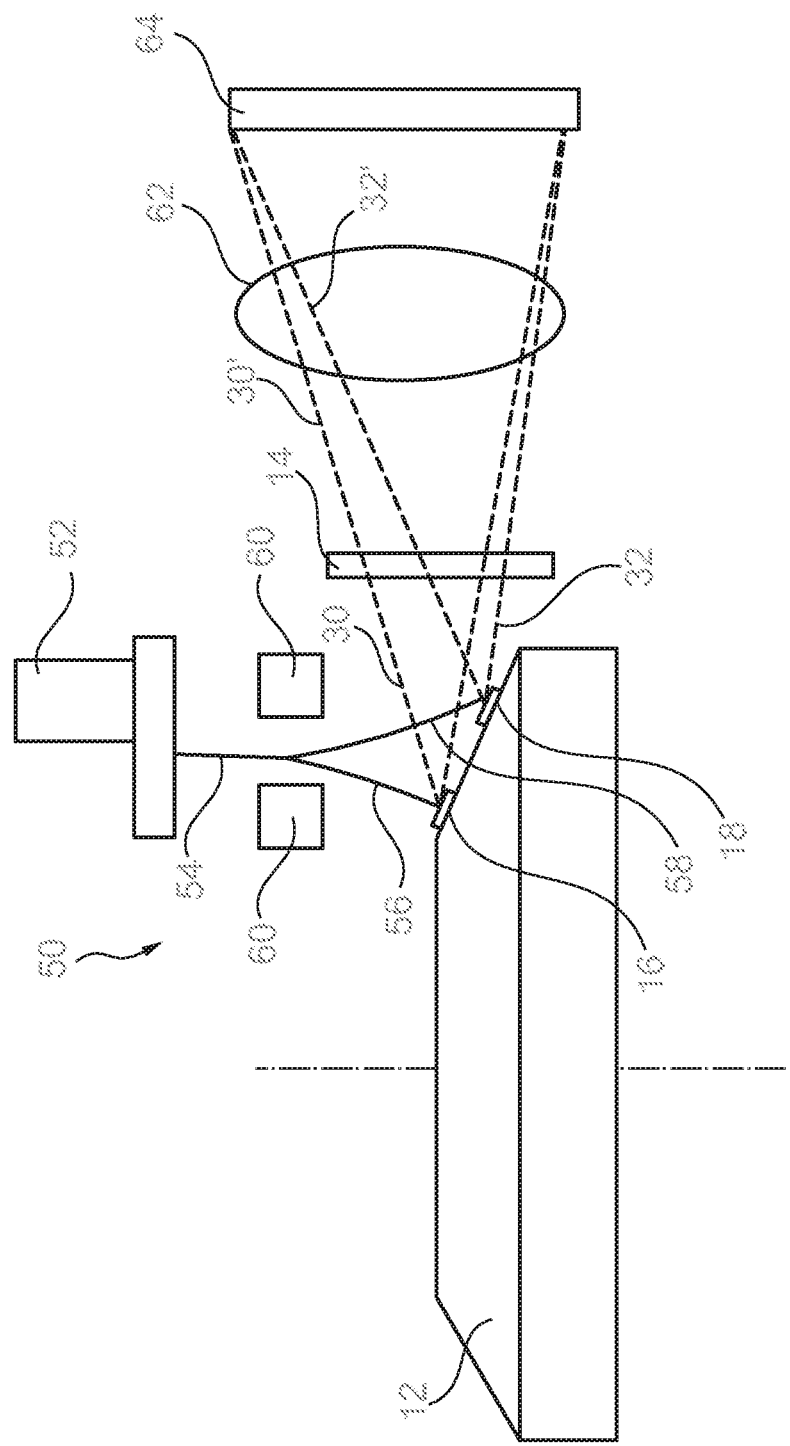
FIG. 5 shows a schematic view of an exemplary embodiment of a dual-energy X-ray tube according to the present invention.

According to a further exemplary embodiment, shown in FIG. 5, the X-ray tube is a dual-energy tube 50, comprising a cathode arrangement 52, which is configured to provide an electron beam 54, i.e. a beam of accelerated electrons. The cathode arrangement 52 is further adapted to provide the electron beam 54 as a first electron beam 56 accelerated with a first voltage difference between anode and cathode to the first focal spot position 16, and as a second electron beam 58 accelerated with a second voltage difference between anode and cathode to the second focal spot position 18. The first voltage may be lower than the second voltage.

According to a further exemplary embodiment, not shown, the tube current (mA) may also be controlled for the two locations. For example, in case of only switch voltage the tube current will drop with the lower voltage. However, for an improvement from an imaging standpoint, the tube current is also adjusted for the spot locations, as well as the voltage. This may also be applied with two track materials.

For example, a deflection arrangement 60 can be provided in order to deflect the electron beam 54 such that in case the first voltage is applied, the electron beam 54 is directed towards the first focal spot position 16, and in case the electron beam is provided with the second voltage, the deflection arrangement ensures that the electron beam 54 is directed towards the second focal spot position 18.

The deflection arrangement and subsequent focal spot positions coupled with the filter described, allow for fast switching between a filtered and unfiltered beam.

Thus, the first X-ray radiation 30 is provided with a lower energy than the second X-ray radiation 32.

According to the exemplary embodiment shown in FIG. 4, the filter unit 14 is provided such that the second filtering characteristics are adapted to remove low energy photons from the second voltage beam, i.e. from the second X-ray radiation 32 resulting from the higher voltage electron beam. Thus, the second X-ray radiation, or second X-ray beam 32, passes the filter unit 14 as a further enhanced, i.e. differentiated, second X-ray beam 32'. In case the first filtering characteristics are provided as to apply no filtering effect to the first X-ray beam 30, the first X-ray beam 30 leaves the filter unit 14, i.e. after passing the filter unit 14, as a first X-ray beam 30', which has the same characteristics as the first X-ray beam 30, or at least essentially the same X-ray characteristics.

According to a further exemplary embodiment, some filtering of the first X-ray beam is provided, since some of it will pass through the filter material. However, the filtering applies to only part of the first X-ray beam, whereas for the other position, i.e. the second focal spot position, the filtering applies to more of the beam, e.g. the complete beam.

However, since the filter provides a removal of low energy photons from the second X-ray beam 32, the thus resulting second X-ray beam 32' is further differentiated from the lower energy X-ray beam 30'.

As schematically indicated, and not illustrated in scale, an object 62 can be provided between the X-ray tube according to the present invention and a detector 64, such that the object 62 can be radiated with different X-ray energy beams.

The X-ray radiation produced by an X-ray tube contains photons of more than one energy. The characteristic Bremsstrahlung depends on the electron accelerating voltage (kV) and material in which the X-rays are produced (target). The X-ray beam will contain photons with energies up to the accelerating voltage (kV) used. Since there will be considerable overlap in the spectra of two beams, even generated with different kV's, by filtering out the lower energy X-rays of the higher energy beam we can have a greater difference in the two beams.

According to the present invention, the term "low energy photons" refers to photons with energies lower than the lower accelerating voltage (kV).

For example, the second voltage beam 58 is a high voltage beam. The term "high voltage beam" refers to a minimal kV depending on the application. For example, for analytical work it could go as low as 3 kV; for medical imaging the range can be provided to be 20 kV to 150 kV; for CT, the use of 80 kV and 140 kV is provided. The lower range may be 60 to 80 kV and the higher range may be 120 to 140 kV. Of course, other values can also be applied.

According to the present invention, the dual-energy tube may be provided as a multiple-energy tube, wherein electron beams with more than two voltages are provided (not further shown).

As shown in FIG. 6a, according to an exemplary embodiment of the invention, the first portions 24 are provided with lateral faces 66, which are aligned to a common reference point 68, as indicated with dotted connection lines 70 for an upper and lower lateral face of the respective first portion. Of course, this can be provided in the x direction or z direction or in both directions. The common reference point is preferably the first focal spot position 16, in order to provide a directional filtering of the respective X-ray beam emanating from the first focal spot position 16, and thus providing a maximum quantity or percentage of the first X-ray beam radiation passing through the filter unit 14 via the first portions 24.

According to a further exemplary embodiment of the invention, since the second portions 28 provided between adjacent first portions 24 also mean at least a certain filtering of a minor part of the X-ray radiation from the first X-ray beam 30 to be filtered on behalf of the second filtering characteristic of the second portions 28, it is possible to store a filter image, i.e. a respective image of the filter as provided by a first X-ray beam 30. The filter image can then later be subtracted from actual or current images to consider the respective filtering effect, even though it is only a minimum filter effect.

It is further noted that throughout the embodiment shown in the figures, the dimensions and proportions of the first and second portions are not shown in a realistic manner, in order to ensure a better readability of the figures. In particular, the second portions can be provided in much narrower or much broader pattern, and also the distance between the second portions, i.e. the width of the first portions can be provided in a broader or narrower pattern.

As mentioned before, the first X-ray beam is at least partly only affected by the first filtering characteristics. Contrary to this, the second X-ray beam is affected by the second filtering characteristics throughout the beam width.

Figure 6B:
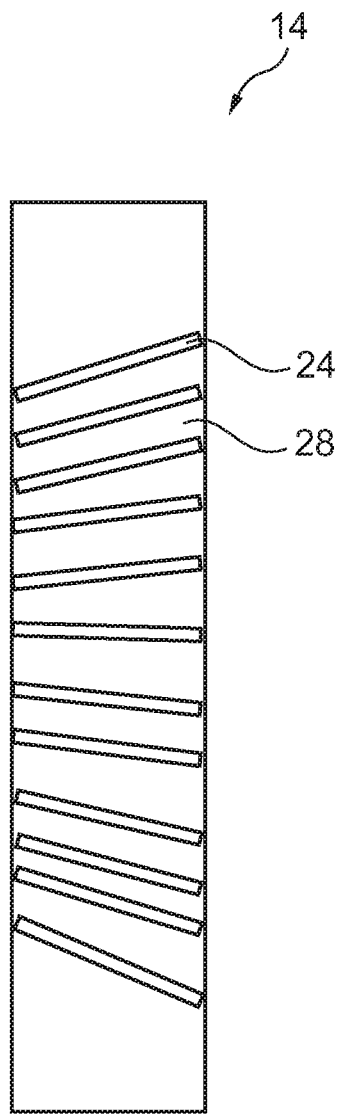

As shown in FIG. 6b, according to a further exemplary embodiment of the invention, the first portions 24 are provided as rather narrow slots between the second portions 28 which are provided as broader sections separating adjacent first portions.

For example, the first portions are holes or slots in a filter body.

Figure 7:
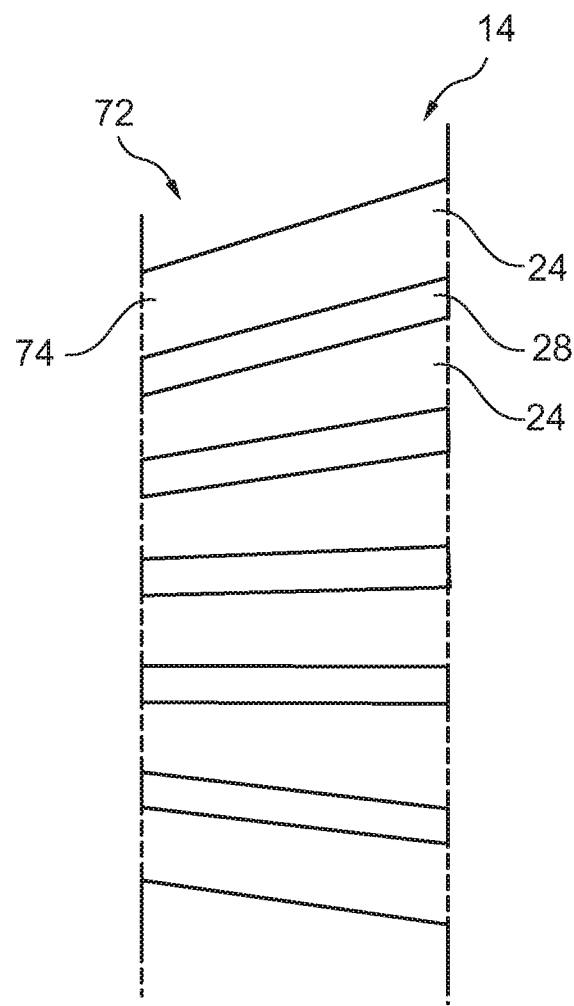

As shown in FIG. 7, according to a further exemplary embodiment, the filter unit 14 comprises a filter body structure 72 which is provided with the second filtering characteristics, and first portions 24 are provided as recesses 74 in the filter body structure. As can be seen, the recesses 74 are provided as openings or through-holes or through openings. Thus, the parts of the filter body structure 72 arranged between adjacent first portions 24 form the second portions 28.

For example, the recesses are unfilled. The recesses may also be filled with a filling material, which is provided with the first filtering characteristics.

For example, the filling material may be non-filtering to X-ray radiation. The filling material may also have a filtering effect which is different than the filtering effect of the body structure.

Figure 8:
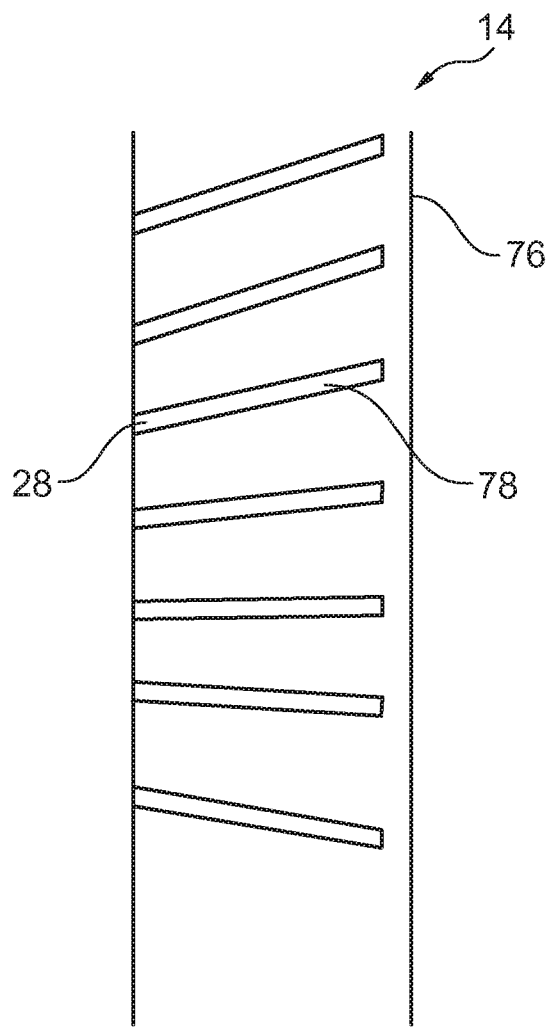

According to a further exemplary embodiment, shown in FIG. 8, the filter unit 14 comprises a first body structure 76, which is provided with the first filtering characteristics, and the second portions 28 are provided as recesses 78 in the first body structure 76. In order to ensure the filtering with second filtering characteristics, the recesses 78 are filled with a material provided with the second filtering characteristics.

According to a further exemplary embodiment of the invention, as indicated in the above described figures, the first portions are arranged in a fan-shaped manner in the cross-section in at least one direction.

For example, in case of an offset in x- and z-direction, a filter body structure can be provided, in which the first portions 24 are arranged as a plurality of openings, for example bores, that are adapted in their extension direction, and also in their cross-sectional shape to provide a fan-shaped structure in two directions.

According to a further aspect of the invention (although not shown), the second portions 28 may be provided varying in their filtering characteristics in the offset direction. For example, the second portions may vary in their thickness in the offset direction.

The first portions and the second portions may be provided in an alternating manner. The second portions may also be provided as wall segments separating the first portions from each other, wherein, in the cross-section, the wall segments are aligned with the first focal spot position, as already mentioned above.

According to a further example, not shown, a filter structure is made out of a material that has little filtering and another filtering material that provides more attenuation for low energy X-rays is embedded into the first material in various patterns to provide the directional filtering.

Figure 9:
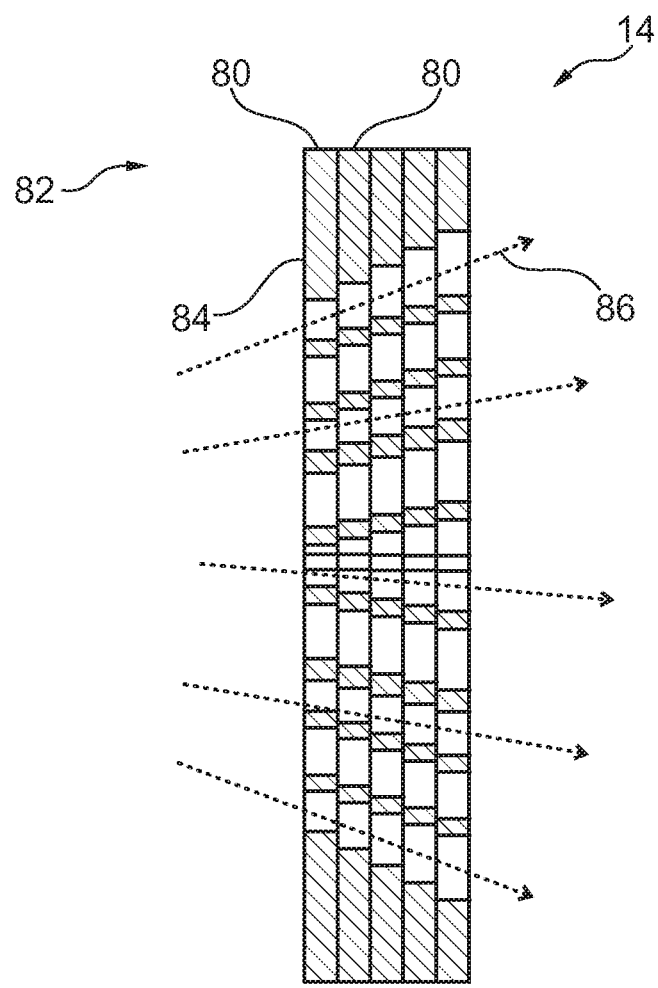

With reference to FIG. 9, according to an exemplary embodiment of the invention, the filter unit 14 comprises a plurality of filter sheets 80 arranged in a staple 82 in the direction of the X-ray radiation. The filter sheets are each provided with a plurality of first sub-portions 84 aligned with the first sub-portions of adjacent filter sheets.

With respect to the term "aligned", it must be noted that the alignment can be provided as shown in FIG. 9, where the respective first sub-portions 84 are provided in a rectangular manner with respect to the surface plane of the respective filter sheet 80. However, the adjacent first sub-portion 84 is aligned with respect to a so-to-speak average through direction, as indicated with dotted arrow 86, while providing a stepped sidewall arrangement due to the respective adding of adjacent sheets. However, the overall alignment provides a continuous through-hole opening to allow a passing of the respective first X-ray beam 30.

According to a further example, not shown, the first sub-portions 84 are provided with respectively inclined sidewalls, thus providing a continuous side surface.

Thus, the first sub-portions of the filter sheets all face the same location, independently whether their microstructure provides rectangular sidewalls of the first sub-portions 84 or respectively being inclined sidewalls.

Figure 10:
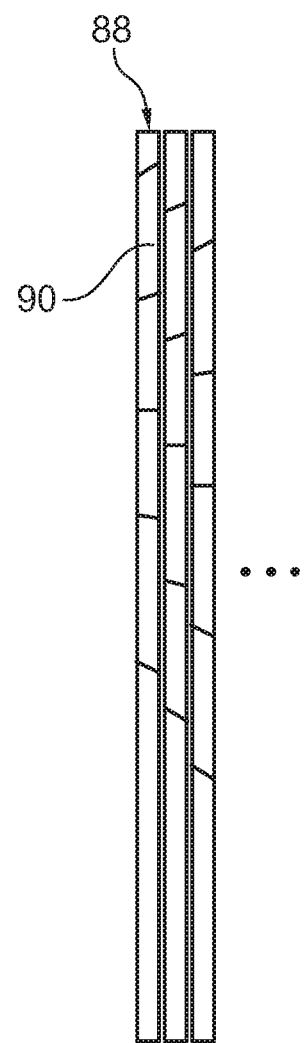

FIG. 10 shows a further exemplary embodiment, wherein for a filter with a non-planar surface, a plurality of filter sheets 88 is provided with a plurality of first sub-portions 90 which are offset to the first sub-portions of adjacent filter sheets, which filter sheets are stacked and then formed to a non-planar surface, for example to provide a curved filter.

The first sub-portions 90 shown in FIG. 10 are provided with inclined surfaces, whereas FIG. 11 shows a plurality of filter sheets 92 with a plurality of first sub-portions 94 with rectangular sidewalls.

However, independently whether the sidewalls are inclined or rectangular, FIG. 11 shows that by bringing the stacked filter sheets into a curved form 96, the respective first sub-portions are then provided in an aligned manner, where the initial offset, as shown in the left half of FIG. 11, is eliminated, due to the different bending radii and bending lengths of the respective filter sheets 92.

According to a further example, thin sheets with directional holes or slots are offset to each other, where holes or slots do not line up from sheet to sheet, but still face the same location. They are then stacked to create the filter. In such case, there would be less of a dose modulation pattern seen by the detectors. The sheets can be made with holes straight through, then stacked offset to each other, then curved, in order to ensure the alignment of the holes or slots.

According to a further example, holes or slots could be provided straight through a filter body, and then later the filter can be formed to point the holes or slots at the first focal spot position.

Figure 13:
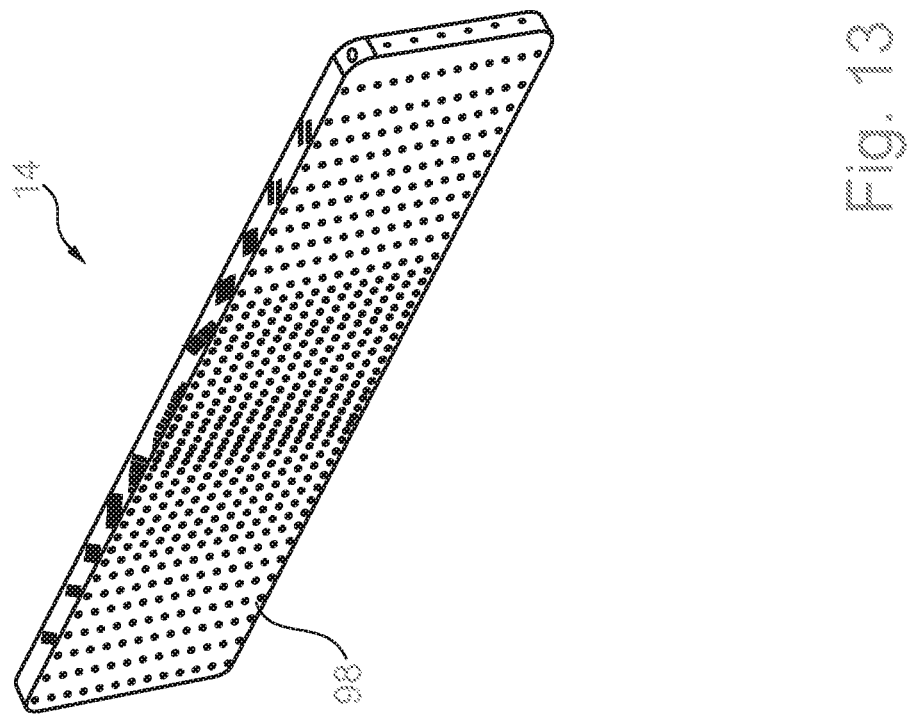
Figure 12:
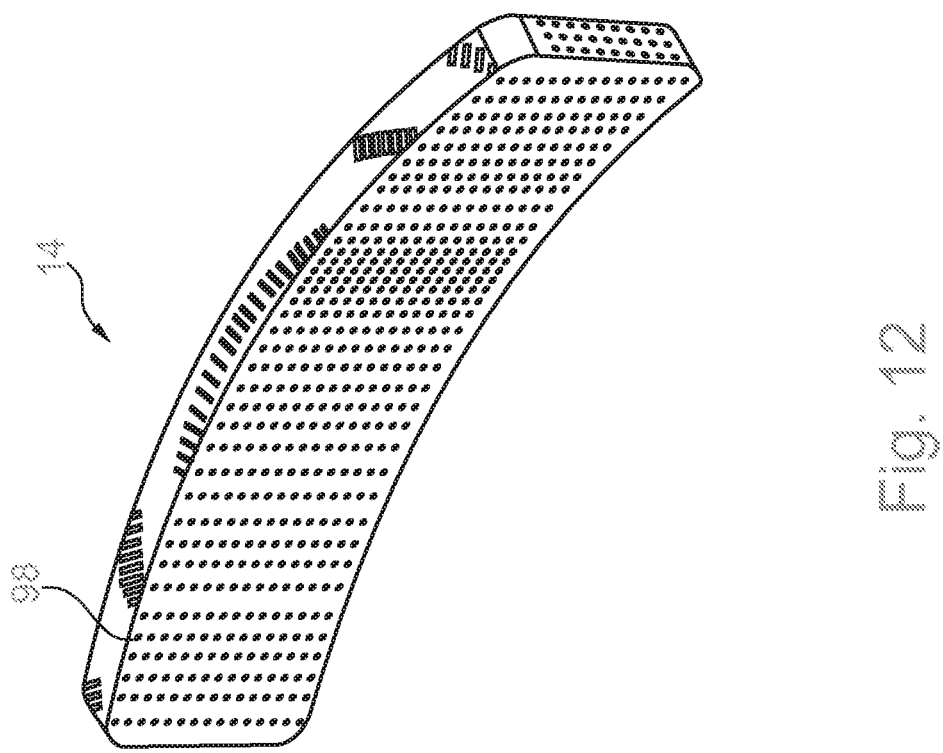

According to further exemplary embodiments of the invention, as shown in FIGS. 12 to 14, the first portions 24 may be provided as holes 98, as shown in FIGS. 12 and 13.

The first portions 24 may also be provided as slots 100 in the first body, as shown in FIG. 14.

The first portions 24 may be provided with a linear geometry. The first portions 24 may also be provided with a two-dimensional geometry with a conical shape pointing to the centre of the first focal spot position 16.

The spacing of the openings may be changed along the length or the width of the filter, i.e. across the filter plane.

For example, FIG. 12 shows a plurality of holes 98, which are adapted in their distance to each other along the width of the filter and the length of the filter.

The filter unit shown in FIG. 12 is shown as a curved filter unit, whereas the filter unit 14 shown in FIG. 13 is provided as a flat filter unit. The holes 98 in FIG. 13 are also provided with a changing spacing across the filter plane.

According to a further exemplary embodiment (not shown), the size, form of the first portions 24 is changed along the length and/or the width of the filter, i.e. across the filter plane.

The cross-section of the first portions 24 can also be changed along the depth of the filter, i.e. in the X-ray radiation projection direction. For example, it is thus possible to provide the first portion 24 as conical portions, in order to provide the second portion 28 as bore portions with parallel sidewalls, thus ensuring a minimum filtering effect for the first focal spot position radiation.

Figure 15:
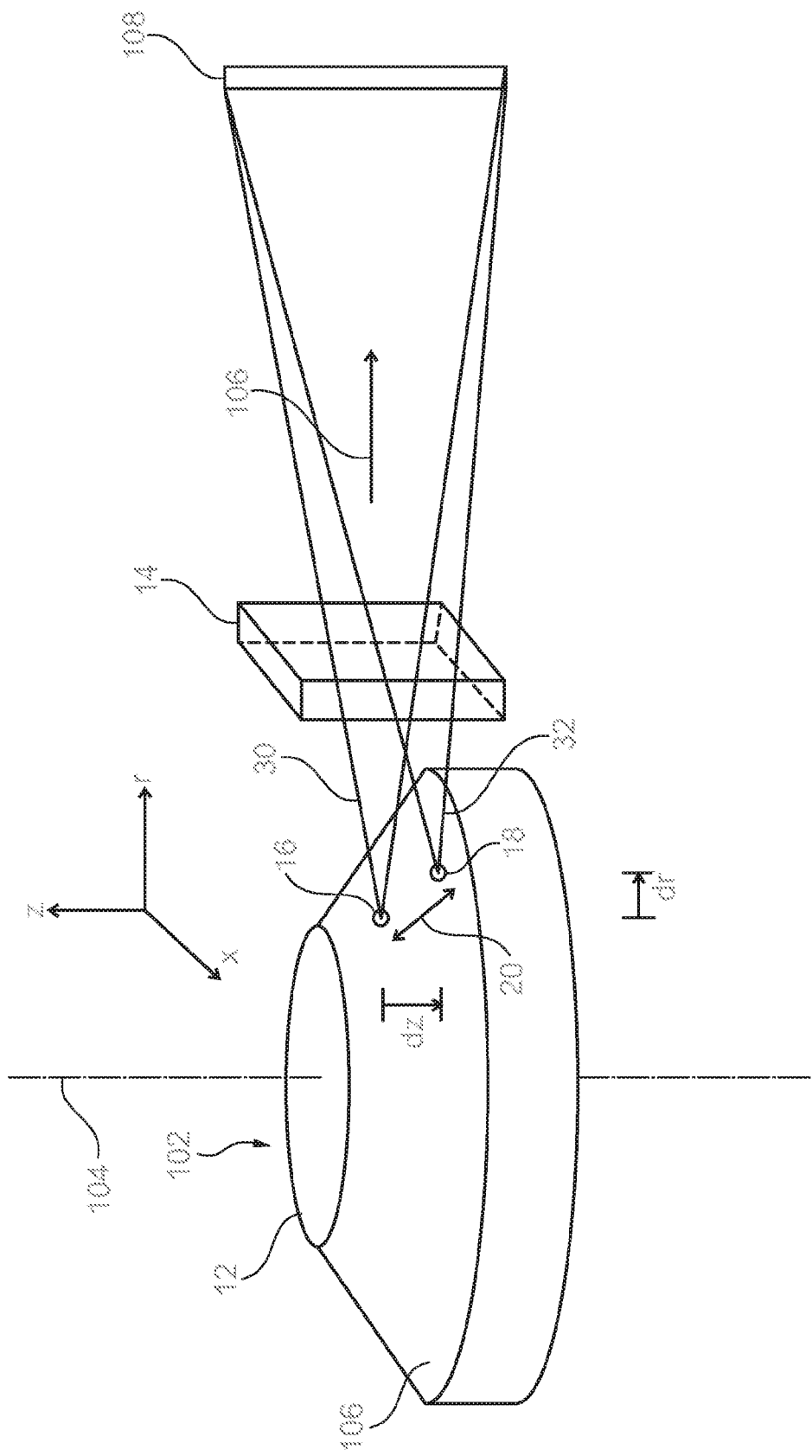
FIG. 15 shows an X-ray tube with a rotating anode according to an exemplary embodiment of the present invention.

FIG. 15 shows a further exemplary embodiment of the invention, wherein the anode 12 is a rotating anode 102 with a rotation axis 104. The X-ray beam, i.e. the first X-ray beam 30 and the second X-ray beam 32, is emitted in a radiation direction 106, as indicated with an arrow, which is perpendicular to the rotation axis 104.

A coordinate system is shown indicating that the rotation axis 104 is also referred to as the z-axis, the radiation direction 106 is referred to as r-axis, and the axis perpendicular to the both before mentioned axes is referred to as x-axis.

Further, the first and second focal spot positions 16 and 18 are indicated, as well as a double arrow 20 indicating the offset. The second focal spot position 18 is offset to the first focal spot position 16 in a first offset direction $d_z$, which is perpendicular to the X-ray radiation projection direction r 106 and parallel to the rotation axis z 104.

In the exemplary embodiment shown in FIG. 15, the two focal spot positions 16, 18 are provided on inclined surface 107 of the rotation anode 102. Thus, the first offset in the first offset direction $d_z$ also includes or results in an offset in further offset direction $d_R$, which does not contribute to the directional filtering effect, or at least only very little, if it would be applied solely.

The filter unit 14 is only schematically indicated, as is also the case for a detector 108, indicated with a frame instead of an arc or square-like form seen in perspective. According to the invention, an object can be arranged between the filter unit and the detector. It must be noted that the filer unit is allocated, or assigned, to the X-ray tube.

Figure 16:
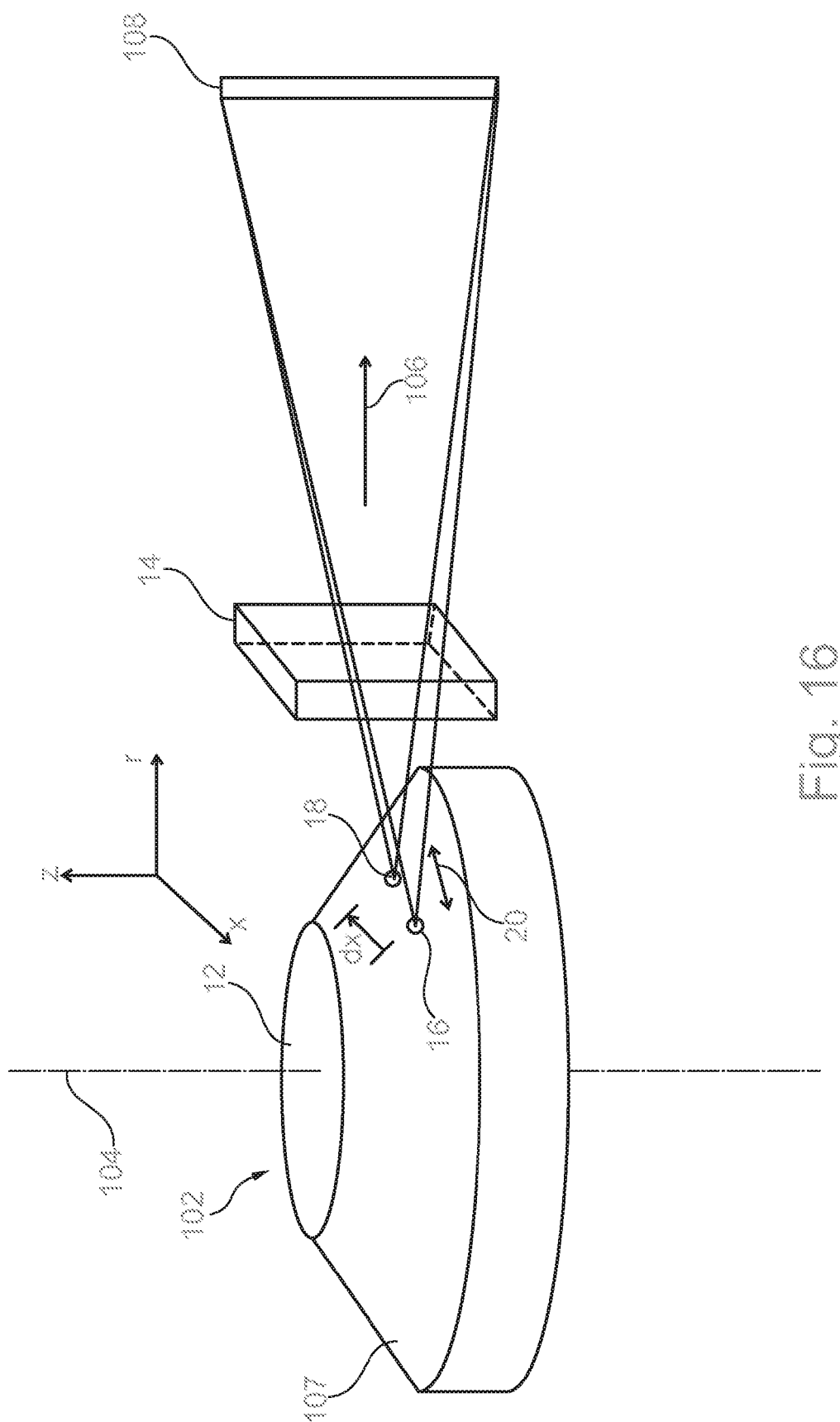
FIG. 16 shows a further exemplary embodiment of a rotating X-ray anode tube.

FIG. 16 shows a further exemplary embodiment, in which the anode is the rotating anode 102. The second focal spot position is offset to the first focal spot position 16, as indicated with double arrow 20, in a second offset direction $d_X$, which is perpendicular to the rotating axis z 104, and perpendicular to the emitting direction r 106.

According to a further exemplary embodiment (not shown), the offset is provided in the first offset direction $d_X$ and the second offset direction $d_Z$.

Figure 17:
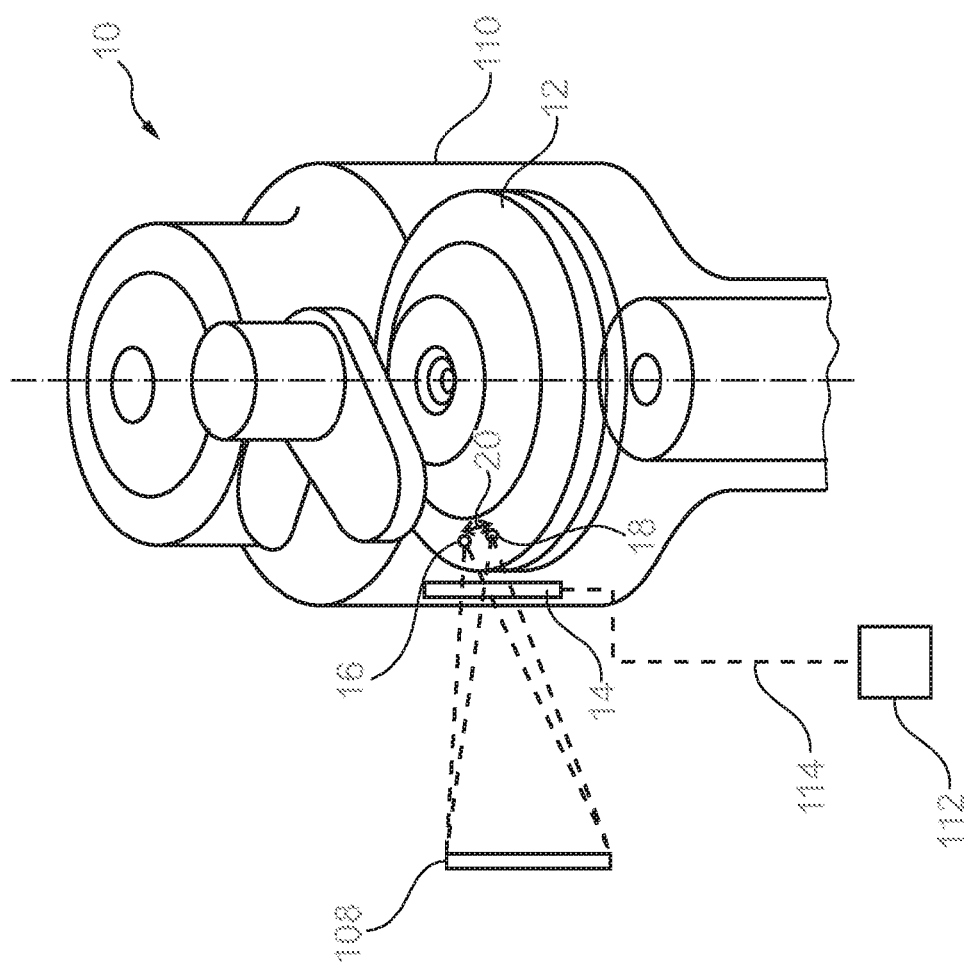
FIG. 17 shows a further exemplary embodiment of an X-ray tube according to the present invention.

FIG. 17 shows a further exemplary embodiment, in which the X-ray tube 10 comprises an envelope 110, in which the anode 12 is provided. The filter unit 14 is arranged inside the envelope. Further, FIG. 17 shows the first and second focal spot positions 16 and 18, being displaced from each other, as indicated with double arrow 20. However, it must be noted that the shown displacement is only one example, and of course, other displacement directions, as mentioned and described above, can be applied. Further, the detector 108 is only schematically indicated, and is not presented in scale, with respect to size and in particular with respect to the distance to the tube.

It is further noted that the X-ray tube 10 is shown as an X-ray tube with a rotational anode. However, according to the present invention, also different X-ray tube types can be provided, having an envelope, in which the anode, as well as the filter unit, are provided, i.e. they are arranged inside the tube.

Further, the filter unit 14 may be provided with a cooling arrangement 112, which is schematically shown with a box only, connected to the filter unit 14 with a dotted connection line, indicating that the cooling is a possible option, but not a necessity for the realization of the present invention.

According to a further exemplary embodiment (not shown), the filter unit 14 can be arranged outside of an X-ray window of the envelope. For example, the filter unit can be provided on the outside of the X-ray window, for example attached to the window's outer surface.

According to a further aspect of the invention, the filter unit 14 is removably fixed in relation to the focal spot positions 16, 18. Thus, for the generation of X-ray radiation with different energies, the filter unit 14 is not moving with respect to the focal spot positions. However, it is possible to provide the filter unit 14 to be removably, for example for cases in which non-dual-energy X-ray radiation of an object is required, or for maintenance purposes.

Figure 18:
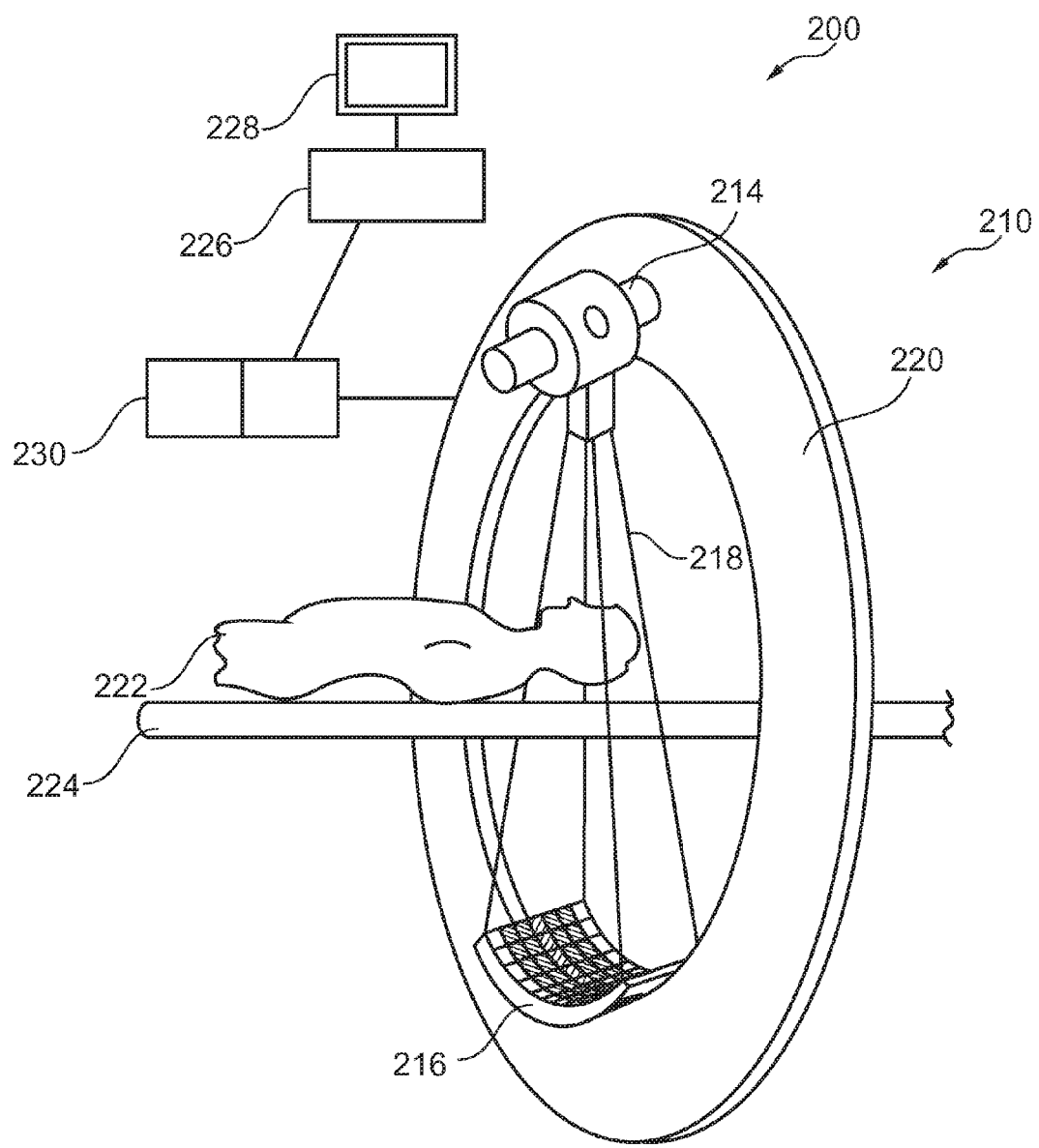
FIG. 18 shows an exemplary embodiment of an X-ray imaging system according to the present invention.
Figure 19:
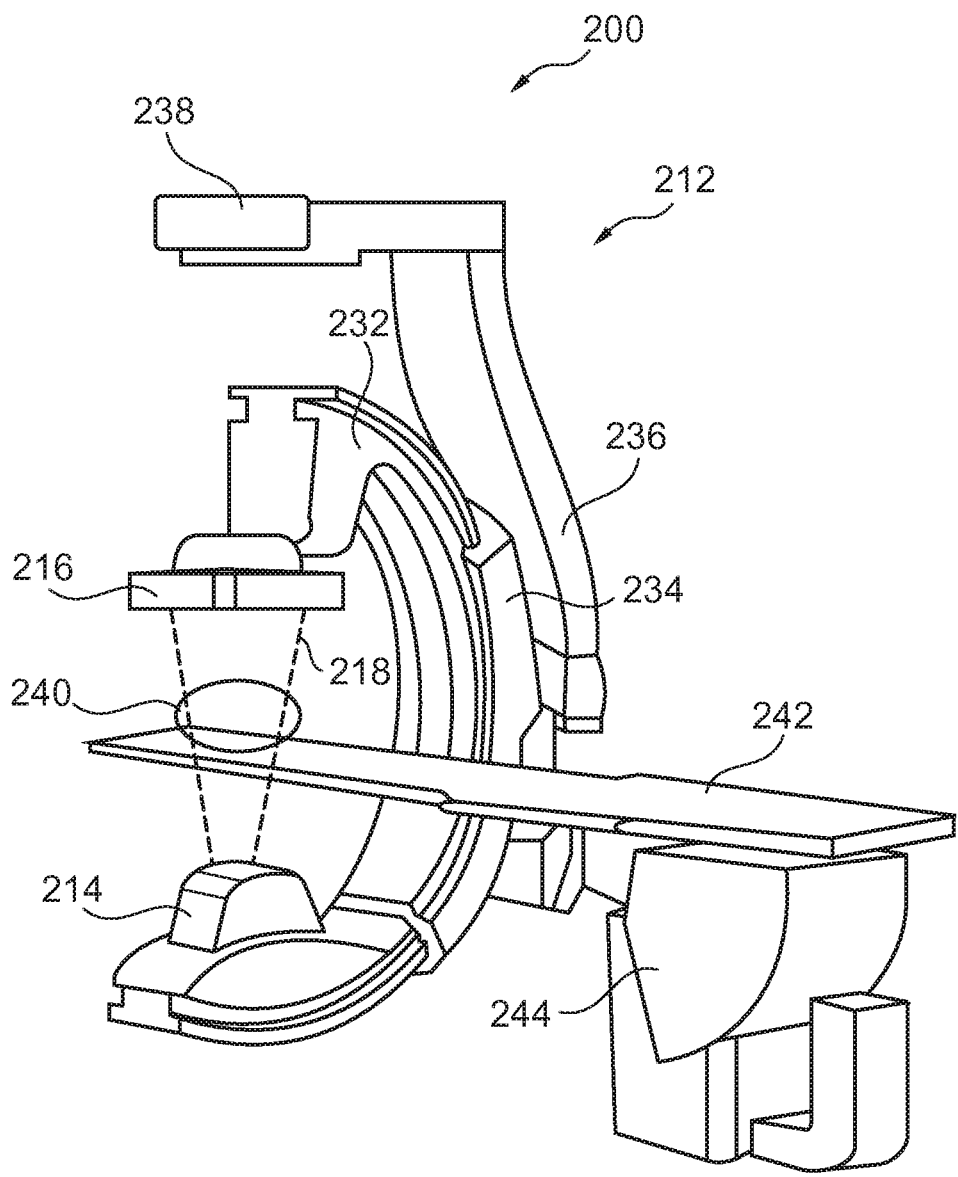
FIG. 19 shows a further exemplary embodiment of an X-ray imaging system according to the present invention.

According to a further exemplary embodiment of the invention, as very schematically shown in FIGS. 18 and 19, an X-ray imaging system 200 is provided, for example a CT system 210 in FIG. 18, or a C-arm system 212 in FIG. 19, comprising an X-ray source 214 and an X-ray detector 216. The X-ray source comprises an X-ray tube according to one of the above-mentioned and described exemplary embodiments. The X-ray detector 216 is adapted to detect X-ray radiation, indicated with symbolic lines 218, resulting from the first X-ray beam emanating from the first focal spot position, and from the second X-ray beam emanating from the second focal spot position. It is noted that no further differentiation is made in FIGS. 18 and 19 with respect to the first and second X-ray beam due to a better understanding of the drawing.

The CT system 210 may comprise a gantry 220, which allows a rotational movement of the X-ray source 214 together with the detector 216. Thus, an object 222, for example a patient, can be provided on a support 224 to allow an adjustment of the object in relation to the X-ray source 214 and the detector 216, as well as a movement with respect to the X-ray source and the detector. Further, a processing unit 226 as well as a display 228 are schematically indicated, together with an interface unit 230.

The C-arm system 212 in FIG. 19 shows a C-arm structure 232, to which ends the detector 216 and the source 214 are mounted. The C-arm structure 232 is movably held by a support 234, which itself is mounted to a ceiling support arm 236, which is mounted to a ceiling by a mounting support 238. The mounting components as well as the C-arm mounting unit are provided to allow different moving possibilities, in particular rotational movements around the ceiling fixation point as well as around the fixation at the end of the support arm structure 236. The shoe-like C-arm support 234 also allows a sliding movement of the C-arm. Thus, different positions of the C-arm in relation to an object 240, provided on a respective support 242 can be provided. The support 242 may a patient table, which is mounted to an adjustable support 244, to allow sliding and upwards and downwards movements.

According to the present invention, also other X-ray imaging modalities and systems are provided, for example systems with a fixed X-ray tube arrangement, or also systems in which X-ray tube and detector are fixedly mounted.

In particular, the X-ray tube with the direction filter according to the preset invention is provided in a system for scanning goods such as luggage control systems or quality inspection systems.

By providing the X-ray source 214 of the X-ray imaging system 200 with a directional filter unit 14 and a respective relation to at least two focal spot positions, it is possible to acquire X-ray images of an object with different X-ray energies, thus providing different image data and material identification.

Of course, a combination of the above-mentioned features relating to the X-ray tube may be combined in several possibilities, although not explicitly mentioned in the present description. In particular, the directional filter can be combined with different electron beam energies, i.e. different voltages, as is also the case for the combination with different focal track materials. In other words, the directional filter can be combined with the different focal track materials, and/or the different electron beam voltages.

Similar applies for the X-ray imaging systems as exemplarily shown in FIGS. 18 and 19.

Figure 20:
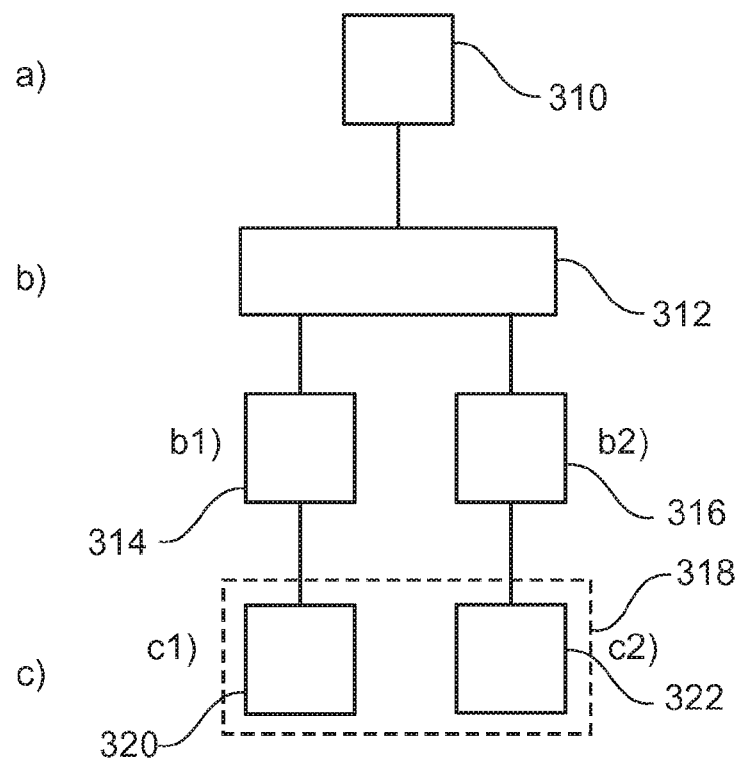
FIG. 20 illustrates basic method steps of an exemplary embodiment of a method for generating a multiple-energy X-ray beam according to the present invention.

In the following, with reference to FIG. 20, the basic steps of a method 300 for generating multiple-energy X-ray beam are described. The method 300 comprises the following steps: In a generation step 310, an electron beam, i.e. a beam of accelerated electrons, is generated. In a direction step 312, the electron beam is directed such that the electron beam impinges at a first focal spot position and at a second focal spot position of an X-ray tube in an alternating manner, wherein, in a first emanating sub-step 314, a first X-ray beam is emanating from the first focal spot position, and in a second emanating sub-step 316, a second X-ray beam is emanating from the second focal spot position. As a further step, a passing step 318 is provided in which the first and second X-ray beam pass through a filter unit. In a respective first passing sub-step 320, at least a first part of the first X-ray beam passes through first portions of the filter unit, and in a second passing sub-step 322, at least a second part of the second X-ray beam passes second portions; wherein the second part of the second X-ray beam is larger than the first part of the first X-ray beam. According to the present invention, the first portions are provided with first filtering characteristics for the X-ray radiation and the second portions are provided with second filtering characteristics for X-ray radiation.

The generation step 310 is also referred to as step a), the direction step 312 as step b), the first emanating sub-step 314 as step b1), the second emanating sub-step 316 as step b2), the passing step 318 as step c), the first passing sub-step 320 as step c1), and the second passing sub-step 332 as step c2).

Figure 21:
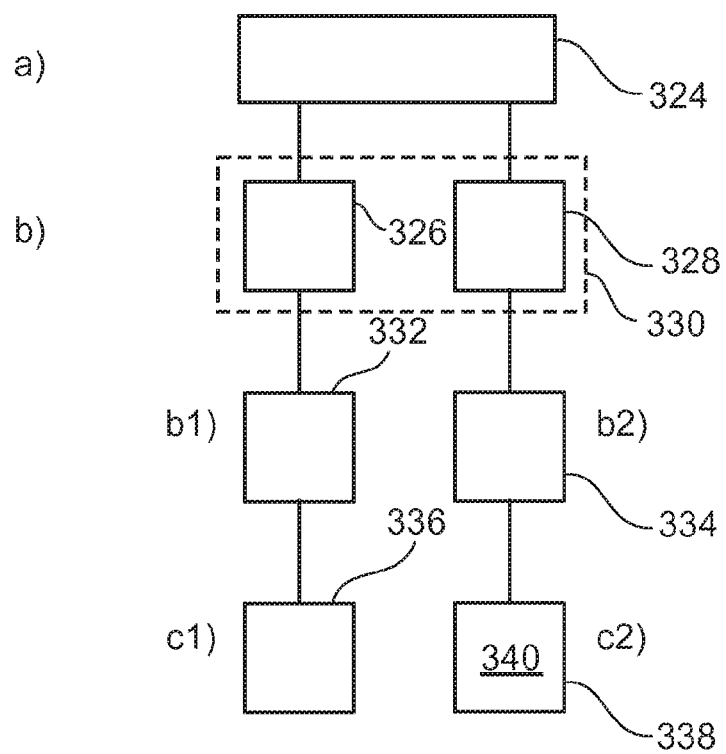
FIG. 21 shows a further exemplary embodiment of a method according to the present invention.

According to a further exemplary embodiment, shown in FIG. 21, in step a), the electron beam is provided as a dual-energy electron beam in a first provision step 324. The electron beam is provided with a first accelerating voltage to the first focal spot and with a second accelerating voltage to the second focal spot, wherein the first voltage is lower than the second voltage. Thus, in step b), the electron beam with a first voltage impinges at the first focal spot position, which is indicated with frame 326, and the second electron beam impinges at the second focal spot position, as indicated with frame 328. The respective direction steps are provided in an alternating manner similar to FIG. 20, which is why a dotted frame 330 is enclosing both sub-steps. Consequently, in step b1), a first X-ray beam with a first energy is emanating in an emanating sub-step 332, whereas in step b2), a second X-ray beam with a second X-ray energy is emanating in a second emanating sub-step 334. Following, in step c1), as a first passing sub-step 336, at least a part of the first X-ray beam with first energy passes through first portions of the filter unit, and in step c2), as a second passing sub-step 338, the second X-ray beam with second X-ray energy passes the second portions. According to the exemplary embodiment shown in FIG. 21, in step c2), the second portions remove low energy photons from the second high voltage beam in a removal 340.

According to a further exemplary embodiment, not shown, specific energy photons are removed, e.g. k-edge filtering.

According to a further exemplary embodiment, not shown, a method is provided in which an image of the filter as being radiated with X-ray radiation from the first focal spot position is acquired and stored. The filter image is then later subtracted from images acquired with radiation from the first focal spot position. Thus, even when, for example, walls of the filter holes or slots filter the X-rays from the first focal spot position, for example from the low kV focal spot position, this can be taken into account for the acquired images.

Further, according to the present invention, a use of a filter unit for the generation of multiple X-ray radiation is provided, wherein the filter unit is provided according to one of the above-mentioned exemplary embodiments.

According to the present invention, it is also provided to combine kV switching and different focal spot materials, in order to provide four different X-ray energies being filtered by the filter unit.

In the following, some further aspects in relation with the present invention are explained. According to the present invention, X-ray beams are generated at different focal spot locations on the target. These locations could contain different target materials and/or different tube kV could be used at each location. As mentioned above, in case of two focal spot locations, and the use of two X-ray tube potentials (kVs), each focal spot location is used with a different kV. Hence, the kV is switched while the focal spot location is switched.

In order to enhance the spectral separation, the X-ray filter is filtering the higher energy beam. By providing the filter as a directional filter, X-rays generated at the first focal spot location, i.e. the low energy beam location, generally pass through unfiltered. However, X-rays generated at another focal spot location, i.e. the higher energy beam location, do not have a line of sight through the slots and are therefore filtered.

According to a further exemplary embodiment, the second filter characteristic varies across the detector plane. This may be a result of the X-ray beam passing through different amounts or different distances of second portions. However, since this is a known relation, the respective detected differences in the detector signals may adjusted accordingly for the detection of the second X-ray beam radiation of an object.

For example, the present invention is in particular applicable for dynamic focal spot (DFS) features used in CT systems. For example, in case of xDFS (Dynamic Focal Spot in X-direction) the resolution can be increased. In the case of zDFS, a virtual doubling of the slice count can result. Of course, xDFS and zDFS can be used simultaneously.

The aspect that the filter does not move relative to the focal spot positions, and thus the X-ray tube, allows fast transitioning times from an unfiltered to filtered X-ray beam, i.e. a transition from one focal spot position to the other, for example in the order of 50 microseconds. Of course, according to the present invention, the transitioning times can also be lower than 10 microseconds. Similar applies to the switching time between kVs. Since the filter itself is not moved between the respective dual-energy radiation steps, fast transitioning and kV switching times can be provided in combination with additional filtering. This also applies for the case of a single energy electron beam without kV switching.

The material for the filter is preferably chosen to remove low energy photons from high kV beam, for example Sn (tin), with respect to the second filtering characteristics.

A further aspect that should be mentioned is that if the filter is focused on the focal spot centre, this provides for a more Gaussian distribution. It is further mentioned that the larger the focal spot position separation is, the better this is with respect to the arrangement of the directional filter unit.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray tube for generating multiple-energy X-ray radiation, with:
    an anode; and
    a directional filter;
    wherein the anode comprises at least a first and a second focal spot position, which are offset from each other in an offset direction transverse to an X-ray radiation projection direction;
    wherein the directional filter comprises a first plurality of first portions with first filtering characteristics for X-ray radiation and a second plurality of second portions with second filtering characteristics for X-ray radiation;
    wherein the filter is a directional filter adapted in a such a way that at least a first part of a first X-ray beam emanating from the first focal spot position passes through the directional filter unit via the first portions; and
    at least a second part of a second X-ray beam emanating from the second focal spot position passes the second portions when passing through the filter unit;
    the directional filter has through-holes or slots, the through-holes or slots being transmissive to first X-ray beam from the first focal spot and pointing at the first focal spot and has separators which are less transmissive to X-rays, the separators being oriented such that the first X-ray beam from the first focal spot passes between the separators through the through-holes or slots and a second X-ray beam from the second focal spot passes obliquely through one or more separators;
    wherein at least a portion of the first X-ray beam and at least a portion of the second X-ray beam pass through a common area of the filter.

2. The X-ray tube according to claim 1, wherein lateral faces of the first portions are aligned to a common reference point; wherein the common reference point is the first focal spot position.

3. The X-ray tube according to claim 1, wherein the X-ray tube is a dual-energy tube comprising a cathode arrangement, which is configured to provide a first electron beam with a first accelerating voltage to the first focal spot position and a second electron beam with a second accelerating voltage to the second focal spot position, wherein the first voltage is lower than the second voltage; and
    wherein the second filter characteristics are adapted to remove low energy photons from the second voltage beam.

4. The X-ray tube according to claim 1, wherein the directional filter comprises a filter body structure, which is provided with the second filtering characteristics; and wherein the first portions are provided as recesses in the filter body structure.

5. The X-ray tube according to claim 1, wherein the second portions vary in their filtering characteristics in the offset direction.

6. The X-ray tube according to claim 1, wherein the directional filter comprises a plurality of filter sheets arranged in a staple in the direction of the X-ray radiation; and
    wherein the filter sheets are each provided with a plurality of first sub-portions aligned with the first sub-portions of adjacent filter sheets.

7. The X-ray tube according to claim 1, wherein the anode is a rotating anode with a rotation axis (z); and wherein the X-ray beam is emitted in a direction (r) perpendicular to the rotation axis;
    wherein the second focal spot position is offset to the first focal spot position in a first offset direction ($d_z$), which is perpendicular to the X-ray radiation projection direction (r) and parallel to the rotation axis (z); and/or in a second offset direction ($d_x$), which is perpendicular to the rotation axis (z) and perpendicular to the emitting direction (r).

8. The X-ray tube according to claim 1, wherein the X-ray tube comprises an envelope; and wherein the directional filter arranged inside the envelope or outside of an X-ray window of the envelope.

9. An X-ray imaging system, comprising:
    an X-ray source; and
    an X-ray detector;
    wherein the X-ray source comprises the X-ray tube according to claim 1; and
    wherein the X-ray detector is adapted to detect X-ray radiation resulting from the first X-ray beam emanating from the first focal spot position, and from the second X-ray beam emanating from the second focal spot position.

10. A method for generating a multiple-energy X-ray beam, comprising the following steps:
- a) generating an electron beam;
- b) directing the electron beam such that the electron beam impinges at a first focal spot position and at a second focal spot position of an X-ray tube in an alternating manner; wherein
  - b1) a first X-ray beam emanates from the first focal spot position; and
  - b2) a second X-ray beam emanates from the second focal spot position;
- c) passing of the first and second X-ray beam through a directional filter; wherein
  - c1) at least a first part of the first X-ray beam passes through first portions of the directional filter; and
  - c2) at least a second part of the second X-ray beam passes through second portions of the directional filter unit;
- wherein a portion of the parts of the first X-ray beam, which pass through the directional filter via the first portions, and a portion of the second X-ray beam, which passes the second portions when passing through the directional filter, pass through a common area of the directional filter for radiating an object;
- the directional filter has through-holes or slots being substantially transmissible for X-ray beams from the first focal spot and pointing at the first focal spot and separators being to some extent transmissible for radiation from the second focal spot wherein the two X-ray beams hit the directional filter at different angles; and
- wherein the first portions are provided with first filtering characteristics for the X-ray radiation and the second portions are provided with second filtering characteristics for X-ray radiation.

11. The method according to claim 10,
- wherein in step a), the electron beam is provided as a dual-energy electron beam with a first accelerating voltage to the first focal spot and with a second accelerating voltage to the second focal spot; wherein the first voltage is lower than the second voltage; and
- wherein in step c2), the second portions remove low energy photons from the second X-ray beam.

12. An X-ray tube for generating multiple-energy X-ray radiation with:
- an anode;
- a cathode assembly configured to generate and accelerate an electron beam to first and second displaced positions of the anode to define first and second focal spots displaced by an offset;
- a directional filter having a plurality of first portions and at least one second portion, the first portions having first X-ray filtering characteristics, and the second portion having second X-ray filtering characteristics, the second filter characteristics being different from the first X-ray filtering characteristics, the first and second portions having lateral faces which converge towards and align with the first focal spot such that X-rays emitted by the first focal spot travel directly through the first portions and are filtered with the first filtering characteristics and X-rays emitted by the second focal spot travel obliquely to the lateral faces through the first and second portions to be filtered with a combination of the first and second filter characteristics.

13. The X-ray tube according to claim 12, wherein the second portions are planar sheets which are thinner than the first portions and attenuate radiation more than the first portions.

14. The X-ray tube according to claim 12, wherein the second portion is a unitary element and the first portions include an array of recesses defined in the second portion.

15. An X-ray imaging system comprising:
- the X-ray tube according to claim 12;
- an X-ray detector;
- a processor configured to receive data from the X-ray detector and process the data into an image; and
- a display device configured to display the image.

16. The X-ray imaging system according to claim 15, wherein the processor is further configured to generate a filter image from filtered X-rays emitted by the first focal spot without an object between the X-ray tube and the detector and subtract the filter image from an image of an imaged object.

* * * * *